US012773461B2

(12) United States Patent
Zhu et al.

(10) Patent No.: US 12,773,461 B2
(45) Date of Patent: Oct. 27, 2026

(54) CAMPTOTHECIN DRUG AND ITS ANTIBODY CONJUGATE THEREOF

(71) Applicant: SICHUAN BAILI PHARMACEUTICAL CO. LTD., ChengDu (CN)

(72) Inventors: Yi Zhu, ChengDu (CN); Weili Wan, ChengDu (CN); Shi Zhuo, ChengDu (CN); Wenfang Qin, ChengDu (CN); Yong Zhang, ChengDu (CN)

(73) Assignee: SYSTIMMUNE, INC., Redmond, WA (US)

( * ) Notice: Subject to any disclaimer, the term of this patent is extended or adjusted under 35 U.S.C. 154(b) by 1050 days.

(21) Appl. No.: 17/601,055

(22) PCT Filed: Sep. 15, 2020

(86) PCT No.: PCT/CN2020/115429
§ 371 (c)(1),
(2) Date: Jul. 6, 2022

(87) PCT Pub. No.: WO2022/056696
PCT Pub. Date: Mar. 24, 2022

(65) Prior Publication Data
US 2022/0378928 A1 Dec. 1, 2022

(51) Int. Cl.
*A61P 35/00* (2006.01)
*A61K 47/68* (2017.01)
*C07D 491/22* (2006.01)
*C07K 16/30* (2006.01)

(52) U.S. Cl.
CPC .... *A61K 47/6889* (2017.08); *A61K 47/68037* (2023.08); *A61K 47/6851* (2017.08); *A61P 35/00* (2018.01); *C07D 491/22* (2013.01); *C07K 16/30* (2013.01)

(58) Field of Classification Search
CPC . A61P 35/00; A61K 47/6889; A61K 47/6851; A61K 47/68037; C07D 491/22; C07K 16/30
See application file for complete search history.

(56) References Cited

FOREIGN PATENT DOCUMENTS

CA 3114474 A1 * 4/2020 ......... A61K 47/6889

OTHER PUBLICATIONS

Han, Seungmin, et al. "The potential of topoisomerase inhibitor-based antibody-drug conjugates." Pharmaceutics 14.8 (2022): 1707. (Year: 2022).*

Okamoto, Hiromi, et al. "Pharmacokinetics of trastuzumab deruxtecan (T-DXd), a novel anti-HER2 antibody-drug conjugate, in HER2-positive tumour-bearing mice." Xenobiotica 50.10 (2020): 1242-1250. (Year: 2020).*

Perez-Ortega, Heber Uriel, et al. "Camptothecin in Cancer Therapy: Current Challenges and Emerging Strategies with Nanoemulsions." Pharmaceutics 17.11 (2025): 1414. (Year: 2025).*

* cited by examiner

*Primary Examiner* — James H Alstrum-Acevedo
*Assistant Examiner* — Justin Christopher Sanchez
(74) *Attorney, Agent, or Firm* — EpiMED LLC

(57) ABSTRACT

The present application discloses a camptothecin drug and its antibody conjugate. Based on a comprehensive understanding of ADC drugs, the inventor designed a series of active anti-tumor exatecan-derivatives. The designed anti-tumor molecular compound showed good anti-tumor activity in the experiment.

10 Claims, 1 Drawing Sheet

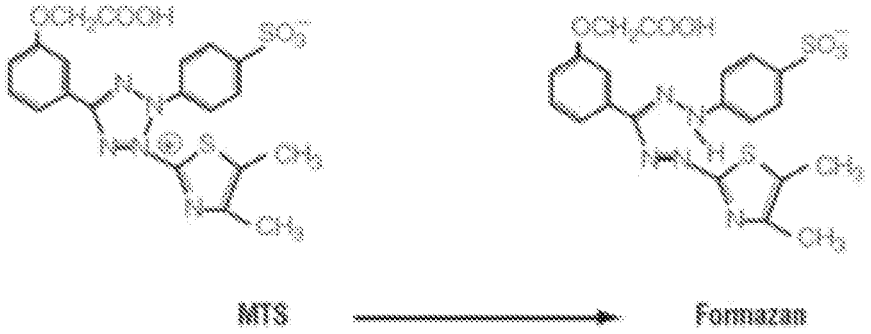
MTS
Formazan

CAMPTOTHECIN DRUG AND ITS ANTIBODY CONJUGATE THEREOF

CROSS REFERENCE TO RELATED APPLICATION

This application is a national stage application of International application number PCT/CN2020/115429, filed Sep. 15, 2020, titled "A Camptothecin Drug And The Antibody Conjugate Thereof," which is hereby incorporated by reference in its entirety.

TECHNICAL FIELD

The application relates to the field of anti-tumor medicine in general, and camptothecin drugs used as anti-tumor drugs and antibody-camptothecin drug conjugates in particular.

BACKGROUND

Antibody-drug conjugates (ADC), as a new type of targeted drugs, generally comprises three parts: antibodies or antibody-like ligands, small-molecule drugs, and linkers that couple the ligands and drugs. Antibody-drug conjugates use the specific recognition of an antibody to an antigen to transport the drug molecules to the vicinity of the target cells and to effectively release the drug molecules to achieve the treatment purpose. In August 2011, the U.S. Food and Drug Administration (FDA) approved the listing of Adecteis™, a new ADC drug developed by Seattle Genetics for the treatment of Hodgkin's lymphoma and recurrent degenerative large cell lymphoma (ALCL), and its clinical application has been shown safety and efficacy of such type of drugs.

Camptothecins, as small molecule compounds with antitumor properties, are known to exhibit anti-tumor effects by inhibiting DNA topoisomerase I, and has been incorporated in anti-cancer drugs of irinotecan, exatecan, and SN38. Many camptothecin drugs have been used in clinical practice, and the main indications are bone cancer, prostate cancer, breast cancer, and pancreatic cancer. Unlike irinotecan in current clinical use, exatecan does not need to be activated by enzymes. In addition, compared with SN-38, which is the pharmacodynamic body of irinotecan, and topotecan, which is also used in clinical practice, exatecan has a stronger inhibitory effect on topoisomerase I activity and has stronger damaging effect against a variety of cancer cells in vitro. In particular, it also shows an effect on cancer cells that show resistance to SN-38 through the expression of P-glycoprotein. Exatecan has not been successfully marketed as a single chemotherapeutic drug, which is speculated to be related to its higher cell activity, resulting in a narrow therapeutic window.

The Antibody-drug conjugate (ADC) drugs have the advantages of increasing water solubility, improving targeting, specific binding of antibodies to antigens carries drugs close to target cells, and effectively killing tumors by releasing drugs near the target cells, and reducing toxic side effects. Camptothecin drugs have considerable application prospects in ADC drugs.

The technical problem the current disclosure aims to solve is to explore and find better and improved anti-tumor camptothecin compounds, to improve the safety and efficacy of anti-tumor small molecule compounds in ADC drug applications, and to obtain an anti-tumor drug with excellent curative effect.

Based on a comprehensive understanding of ADC drugs, the application designed a series of active anti-tumor camptothecin derivatives, and demonstrates through experiments that anti-tumor small molecule compounds display higher anti-tumor activity in cell experiments.

SUMMARY

A camptothecin derivative and its antibody drug conjugate with improved anti-tumor effects is disclosed. An anti-tumor camptothecin compound as shown in formula I or a pharmaceutically acceptable salt-thereof is disclosed.

I

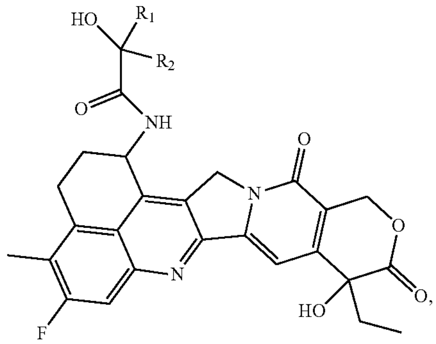

Wherein, $R_1$ and $R_2$ are, at each occurrence, independently selected from the group consisting of $C_1$-$C_3$ alkyl or substituted alkyl, —H, —$CF_3$, aryl, substituted aryl or heteroaryl; or $R_1$ and $R_2$ together with the carbon atoms to which they are attached form cyclobutane, cyclopentane or cyclohexane; and $R_1$ and $R_2$ are not hydrogen at the same time.

In one embodiment, the camptothecin compound or a pharmaceutically acceptable salt thereof has a formula selected from the following formulae (a), (b), or (c):

(a)

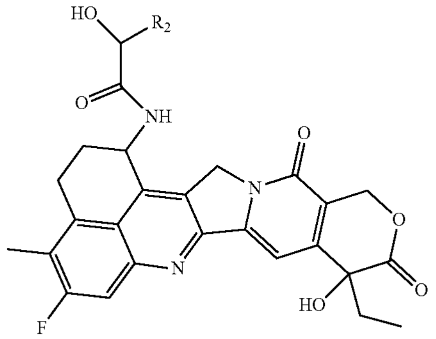

-continued (b)

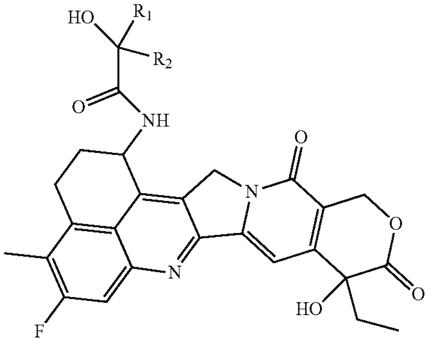

(c)

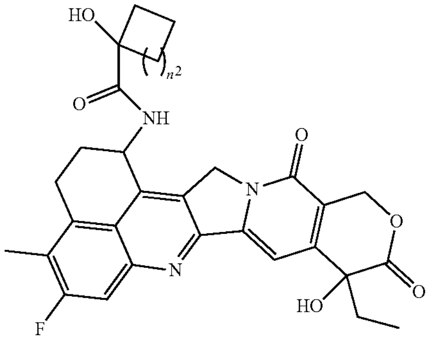

Wherein $R_1$ is hydrogen, $R_2$ is $C_1$-$C_3$ alkyl, —$CF_3$, aryl, substituted aryl or heteroaryl as in formula (a); or $R_1$ and $R_2$ are $C_1$-$C_3$ alkyl, —$CF_3$, aryl, heteroaryl or substituted aryl as in formula (b); or $R_1$ and $R_2$ together with the carbon atoms to which they are connected form cyclobutane, cyclopentane or cyclohexane;

In formula (a), $R_2$ is independently selected from —$(CH_2)n^1$-$CH_3$, —$CF_3$, aryl, heteroaryl, substituted aryl, where $n^1$=0, 1 or 2;

in formula (b), $R_1$ and $R_2$ are independently selected from —$(CH_2)n^1$-$CH_3$, —$CF_3$, aryl, heteroaryl, substituted aryl, where $n^1$=0, 1 or 2;

In formula (c), $R_1$ and $R_2$, together with the carbon atoms to which they are connected form cyclobutane, cyclopentane, or cyclohexane, and $n^2$=1, 2 or 3.

In one embodiment, the camptothecin compound or a pharmaceutically acceptable salt thereof has a formula selected from the following formulae (a-1) or (b-1):

(a-1)

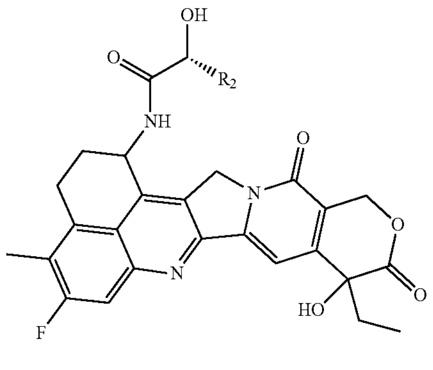

-continued (a-2)

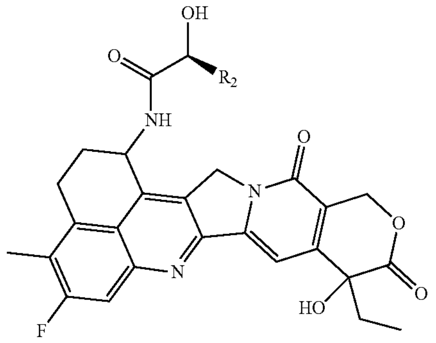

Wherein, $R_1$ is hydrogen, $R_2$ is independently selected from —$(CH_2)n^1$-$CH_3$, —$CF_3$, aryl, heteroaryl or substituted aryl, where $n^1$=0, 1 or 2:

wherein the carbon connected to $R_2$ has two configurations: R or S.

In formula (a-1), the carbon to which $R_2$ is attached is in the R configuration;

In formula (a-2), the carbon to which $R_2$ is attached is in the S configuration.

In one embodiment, the camptothecin compound, or pharmaceutically acceptable salts thereof, comprises the substituted group of aryl group that is selected from the group consisting of halogen, hydrocarbyl, alkoxy, hydroxyl, nitro, amino, hydroxyl and cyano.

In one embodiment, the camptothecin compound, or pharmaceutically acceptable salts thereof, has a formula selected from the following formulae:

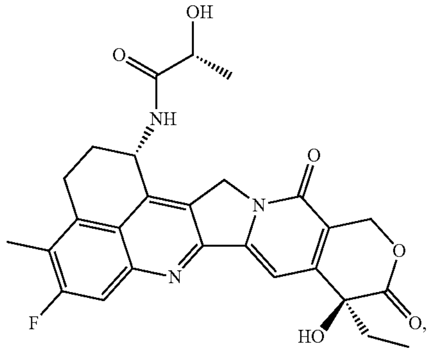

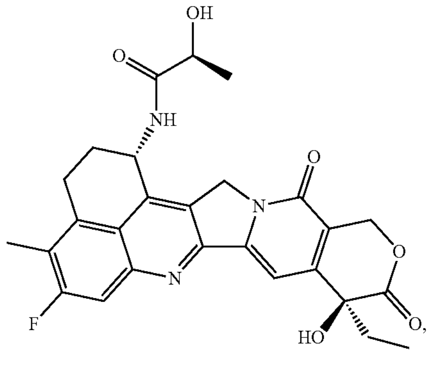

-continued

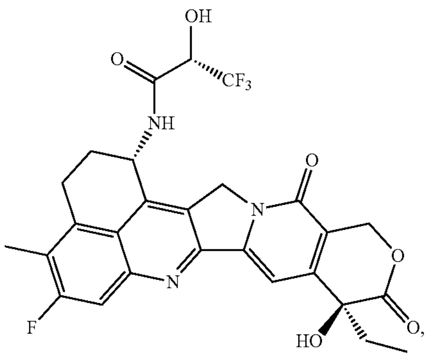

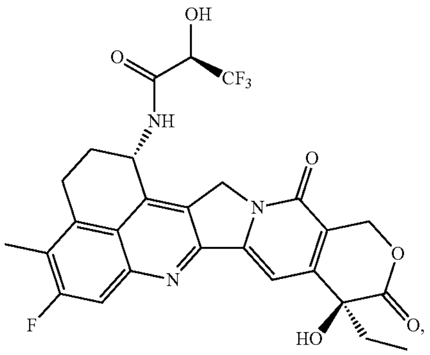

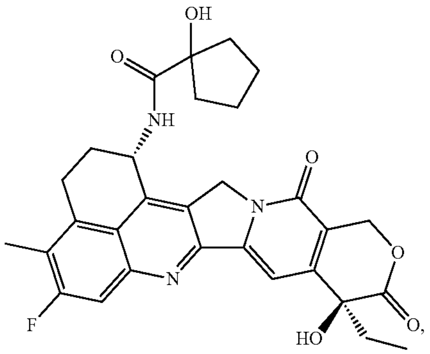

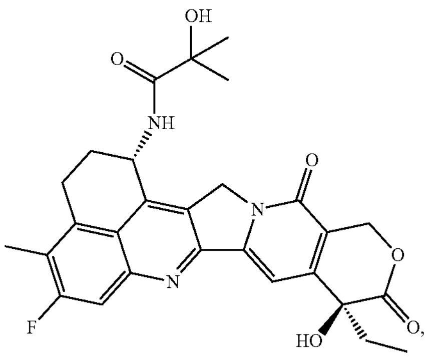

-continued

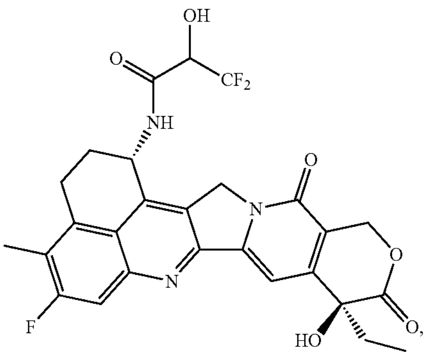

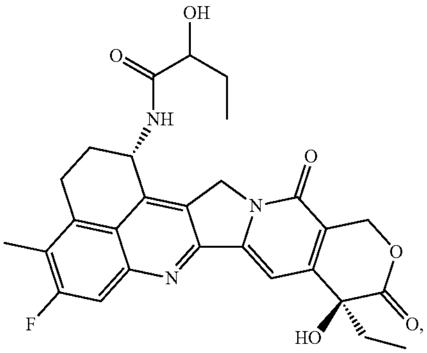

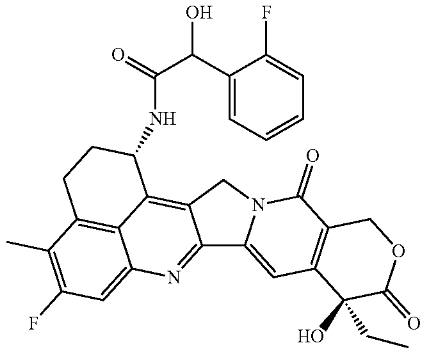

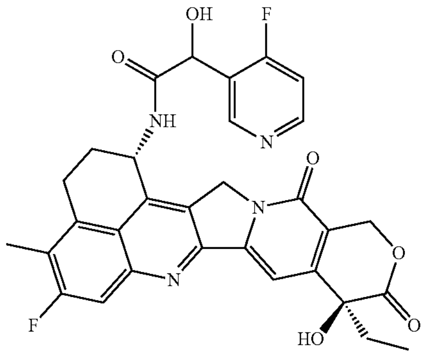

In one embodiment, an antitumor drug comprises the camptothecin compound disclosed, or a pharmaceutically acceptable salt thereof, wherein the antitumor drug is applied in solid tumors or blood tumors including lung cancer, kidney cancer, urethral cancer, colon cancer, rectal cancer, prostate cancer, glioma multiforme, ovarian cancer, pancreatic cancer, breast cancer, melanoma, liver cancer, bladder cancer, gastric cancer, lung cancer or esophageal cancers.

In another embodiment, the application discloses an antibody-drug conjugate shown in formula II, the conjugate exerting its drug effect by releasing a drug (D) after reaching a target cell:

$$Ab-(L-D)_m \qquad (II)$$

wherein Ab is an antibody, an antibody fragment or a protein;

L is an optional connecting unit that is connected to the Ab on one end and connected to the drug (D) on the other end;

D is selected from the described camptothecin compounds or pharmaceutically acceptable salts thereof, connected to L through a hydroxyl group in the D; m is an integer ranging from 1-20.

In one embodiment, in the antibody-drug conjugate, the connecting unit L is selected from the group consisting of —O—, —N(R)$n_1$-, —$CH_2$—, —CH(R)$n_1$-, amide, ester bond, —S—, and -(PEG)$n_2$-, wherein $n_1$ is an integer ranging from 1-3, and $n_2$ is an integer ranging from 1-20.

Another aspect of the present application includes a method of treating a patient in need thereof, comprising administering to the patient the antibody-drug conjugate described above, wherein the patient is afflicted with a tumor, autoimmune disease, or infectious disease, and the antibody of the drug-ligand conjugate specifically binds to a target cell of the cancer, autoimmune disease, or infectious disease.

In one embodiment, an antitumor or anticancer drug comprises the antibody-drug conjugate described above, or pharmaceutically acceptable salts thereof, wherein the drug is used for solid tumors or blood tumors including lung cancer, kidney cancer, urethral cancer, colon cancer, rectal cancer, prostate cancer, glioma multiforme, ovarian cancer, pancreatic cancer, breast cancer, melanoma, liver cancer, bladder cancer, gastric cancer, and esophageal cancer.

DETAILED DESCRIPTION OF THE EMBODIMENTS

Abbreviations and Definitions

Unless otherwise stated, the following terms and phrases as used herein are intended to have the following meanings. When a brand name is used herein, unless the context indicates otherwise, the brand name includes the product formula, generic drugs, and active pharmaceutical ingredients of the brand name product.

The term "alkylene" refers to a divalent linear saturated hydrocarbon group having 1-20 carbon atoms, including groups from 1 to 10 carbon atoms. Examples of alkylene groups include, but are not limited to, methylene (—$CH_2$—), ethylene (—$CH_2$—$CH_2$—), n-propylene, n-butylene, n-pentylene and n-hexylene. Unless otherwise specified, the term "aryl" refers to a polyunsaturated, generally aromatic, hydroxyl group, which can be a single ring or multiple rings (up to three rings) that are fused or covalently linked. The term "heteroaryl" refers to an aryl group (or ring) containing 1-5 heteroatoms selected from N, O, or S, wherein the nitrogen and sulfur atoms are optionally oxidized, and the nitrogen atom is optionally quaternized. Heteroaryl groups can be attached to the rest of the molecule through heteroatoms. Non-limiting examples of aryl groups include phenyl, naphthyl, and diphenyl, while non-limiting examples of heteroaryl groups include: pyridyl, pyridazinyl, pyrazinyl, pyrimindinyl, triazinyl, quinolinyl, quinoxalinyl, quinazolinyl, cinnoline, phthalaziniyl, benzotriazinyl, purinyl, benzimidazolyl, benzopyrazolyl, benzene O-triazolyl, benzisozolyl, isobenzofuranyl, isoindolyl, indazinyl, benzotriazinyl, thienopyridyl, thienopyrimidinyl, pyridopyrimidinyl, imidazopyridine, benzothiaxolyl (benzothiaxolyl), benzofuranyl, benzothienyl, indolyl, quinolinyl, isoquinolinyl, isothiazolyl, pyrazolyl, indazolyl, pteridyl, imidazolyl, Triazolyl, tetrazolyl, oxazolyl, isoxazolyl, thiadiazolyl, pyrrolyl, thiazolyl, furyl, and thienyl, etc. When described as "substituted", the substituents of the above aromatic ring and heteroaromatic ring system are selected from the following acceptable substituents.

Unless otherwise specified in the context, the substituent of the alkyl group can be a variety of groups selected from the following group: -halogen, —OR', —NR'R", —SR', —SiR'R"R'", —OC(O)R', —C(O)R', —$CO_2$R', —CONR'R", —OC(O)NR'R", —NR"C(O)R', —C(O)NR"R'", —NR"C(O)$_2$R', —NH—C($NH_2$)═NH, —NR'C($NH_2$)═NH, —NH—C($NH_2$)═NR', —S(O)R', —S(O)$_2$R', —S(O)$_2$NR'R", —NR'S(O)$_2$R", —CN and —$NO_2$. The number of substituents ranges from 0 to (2m'+1), where m' is the total number of carbon atoms in the group. R', R" and R'" each independently refer to hydrogen, unsubstituted $C_{1-8}$ alkyl, unsubstituted aryl, aryl substituted by 1-3 halogens, unsubstituted $C_{1-8}$ Alkyl, $C_{1-8}$ alkoxy or $C_{1-8}$ thioalkoxy, or unsubstituted aryl-$C_{1-8}$ alkyl. When R' and R" are connected to the same nitrogen atom, they can form a 3-, 4-, 5-, 6- or 7-membered ring together with the nitrogen atom. For example, —NR'R' includes 1-pyrrolidinyl and 4-morpholinyl.

The "derivative" of a compound as used herein refers to a substance that has a chemical structure similar to that of the compound but also contains at least one chemical group that is not present in the compound and/or lacks at least one chemical group that is present in the compound. The compound to which the derivative is compared is called the "parent" compound. Generally, "derivatives" can be produced from the parent compound in one or more chemical reaction steps.

L-Ligand

The ligand unit is a targeting agent that specifically binds to the target part. The ligand can specifically bind to cellular components or to cellular components or to other target molecules of interest. The target moiety or target is usually on the surface of the cell. In some aspects, the role of the ligand unit is to deliver the drug unit to a specific target cell population with which the ligand unit interacts. Ligands include but are not limited to proteins, polypeptides and peptides, as well as non-proteins such as sugars. Suitable ligand units include, for example, antibodies, such as full-length (complete) antibodies and antigen-binding fragments thereof. In embodiments where the ligand unit is a non-antibody targeting agent, it can be a peptide or polypeptide, or a non-protein molecule. Examples of such targeting agents include interferons, lymphokines, hormones, growth factors and colony stimulating factors, vitamins, nutrient transport molecules, or any other cell binding molecules or substances. In some embodiments, the linker is covalently attached to the sulfur atom of the ligand. In some aspects, the sulfur atom is the sulfur atom of a cysteine residue, which forms an interchain disulfide bond of the antibody. In another aspect, the sulfur atom is a sulfur atom of a cysteine residue that has been introduced into the ligand unit, which forms an interchain disulfide bond of the antibody. In another aspect, the sulfur atom is the sulfur atom of the cysteine residue that has been introduced into the ligand unit (for example, by site-directed mutagenesis or chemical reaction). In other aspects, the sulfur atom to which the linker binds is selected from the cysteine residues that form the interchain disulfide bond of the antibody or the frontal cysteine residues that have been introduced into the ligand unit (for example, by site-directed mutagenesis or chemical reaction). In some embodiments, according to the EU index in Kabat (Kabat E A et al., (1991)) "Sequences of proteins of Immunological Interest" (Sequences of proteins of Immunological Interest), fifth edition, NIH publication 91-3242) Numbering system.

As used herein, "antibody" or "antibody unit" includes any part of the structure of an antibody within the scope to which it belongs. This unit can bind, reactively associate, or complex a receptor, antigen, or target other receptor unit possessed by the cell population. The antibody can be any protein or protein molecule that can bind, complex, or react with a part of the cell population to be treated or biologically modified.

The antibody constituting the antibody-drug conjugate of the present application preferably maintains its original antigen-binding ability in the wild state. Therefore, the antibody of the present application can, preferably, specifically bind to the antigen. The antigens involved include, for example, tumor-associated antigens (TAA), cell surface receptor proteins and other cell surface molecules, cell survival regulators, cell proliferation regulators, and molecules related to tissue growth and differentiation (such as known or predicted functional), lymphokines, cytokines, molecules involved in cell cycle regulation, molecules involved in angiogenesis, and molecules related to angiogenesis (such as known or predicted functional). The tumor-related factor may be a cluster differentiation factor (such as CD protein). As described in this application.

Antibodies used in antibody-drug conjugates include, but are not limited to, antibodies directed against cell surface receptors and tumor-associated antigens. Such tumor-associated antigens are well-known in the industry and can be prepared by antibody preparation methods and information well-known in the industry. In order to develop effective cell-level targets that can be used for cancer diagnosis and treatment, researchers are trying to find transmembrane or other tumor-related peptides. These targets can be specifically expressed on the surface of one or more cancer cells, while showing little or no expression on the surface of one or more non-cancer cells. Generally, such tumor-associated polypeptides are more likely to be overexpressed on the surface of cancer cells than on the surface of non-cancer cells. Confirming that such tumor-related factors can greatly improve the specific targeting properties of antibody-based treatment of cancer.

Tumor-associated antigens include, but are not limited to the following tumor-associated antigens (1)-(36). For convenience, the antigen-related information that is well-known in the industry is marked as follows, including name, other names, and gene bank accession number. Nucleic acid and protein sequences corresponding to tumor-associated antigens can be found in public databases, such as Genbank. Antibodies target the corresponding tumor-associated antigens, including all amino acid sequence variants and homologs, and have at least 70%, 80%, 85%, 90%, or 95% homology with the sequence confirmed in the reference, or have the same The tumor-associated antigen sequences in the cited literature have completely identical biological properties and characteristics.

The term "inhibition" or "inhibition of" refers to reducing the detectable amount, or preventing it completely.

The term "cancer" refers to a physiological condition or disease characterized by unregulated cell growth. "Tumor" includes cancer cells.

The term "autoimmune disease" is a disease or disorder that originates from the tissues or proteins of an individual.

The phrase "pharmaceutically acceptable salt" as used herein refers to a pharmaceutically acceptable organic or inorganic salt of a compound (e.g., drug, drug-linker or ligand-linker-drug conjugate). The compound may contain at least one amino or carboxyl group, and therefore may form an addition salt with the corresponding acid or base. Exemplary salts include, but are not limited to: sulfate, trifluoroacetate, citrate, acetate, oxalate, chloride, bromide, iodide, nitrate, bisulfate, phosphate, acid Phosphate, isonicotinate, lactate, salicylate, acid citrate, tartrate, oleate, tannate, pantothenate, bitartrate, ascorbate, salicylate, formate, this format, glutamate, methanesulfonate, ethanesulforiate, benzenesulfonate, p-toluenesulfonate, potassium salt, sodium salt, etc.

In addition, pharmaceutically acceptable salts have more than one point atom in the structure. Examples where multiple charged atoms are part of a pharmaceutically acceptable salt can have multiple counter-examples. For example, a pharmaceutically acceptable salt has one or more charged atoms and/or one or more counter atoms.

According to the mechanism of drug release in cells, as used herein, "linkers" or "linkers of antibody-drug conjugates" can be divided into two categories: non-cleavable linkers and cleavable linkers.

Chemically unstable linkers can be selectively broken due to differences in the properties of plasma and cytoplasm. Such properties include pH, glutathione concentration, etc.

Linkers that are sensitive to pH are often referred to as acid cleavage linkers. Such linkers are relatively stable in the neutral environment of blood (pH 7.3-7.5), but will be affected by weakly acidic endosomes (pH 5.0-6.5) and lysosomes (pH 4.5-5.0). hydrolysis.

Most of the first-generation antibody-drug conjugates use such linkers, such as hydrazones, carbonates, acetals, and ketals. Due to the limited plasma stability of acid-cleavable linkers, antibody-drug conjugates based on such linkers usually have a short half-life (2-3 days). This short half-life limits the application of pH-sensitive linkers in the new generation of antibody-drug conjugates to a certain extent.

For glutathione-sensitive linkers, also known as disulfide bond linkers. Drug release is based on the difference between the high concentration of glutathione in the cell (millimolar range) and the relatively low concentration of glutathione in the blood (micromolar range). This is especially true for tumor cells, whose low oxygen content leads to increased reductase activity, which leads to higher glutathione concentrations. Disulfide bonds are thermodynamically stable, so they have better stability in plasma.

Enzyme-labile linkers, such as peptide linkers, can better control drug release. Peptide linkers can be effectively cut by lysosome proteases, such as cathepsin (Cathepsin B) or plasmin (increased in some tumor tissues). This peptide linkage is considered to be very stable in the plasma circulation. This is because the unsuitable pH value outside the cell and serum protease inhibitors result in the protease usually inactive. In view of high plasma stability and good intracellular cleavage selectivity and effectiveness, enzyme labile linkers are widely used as cleavable linkers for antibody-drug conjugates. Typical enzyme-labile linkers include Val-Cit (vc), Phe-Lys, etc.

Suicide linkers are generally embedded between the cleavable linker and the active drug, or are part of the cleavable linker itself. The mechanism of action of the suicide linker is: when the rupturable linker is broken under suitable conditions, the suicide linker can spontaneously rearrange the structure and release the active drug connected to it. Common suicide linkers include p-aminobenzyl alcohol (PAB) and 6-glucuronide (6-Glucuronide).

The present application will be further elaborated below in conjunction with specific embodiments. It should be understood that these embodiments are only used to illustrate the present application and not to limit the scope of the present application.

The test methods that do not indicate specific conditions in the following examples are usually in accordance with conventional conditions or in accordance with the conditions recommended by the manufacturer. Unless otherwise stated, all percentages, ratios, ratios, or parts are by weight.

Unless otherwise defined, all professions and sciences used in the text have the same meaning as those familiar to those skilled in the art. In addition, any methods and materials similar or equivalent to the content described can be applied to the method of the present application. The implementation methods and materials described in this article are for demonstration purposes only.

Example 1

Synthesis of Compound 2

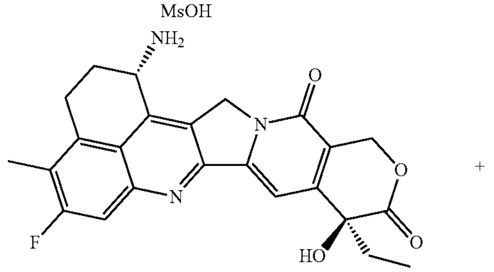

Compound 1

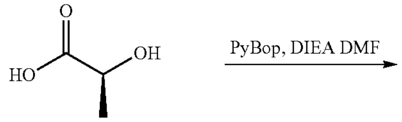

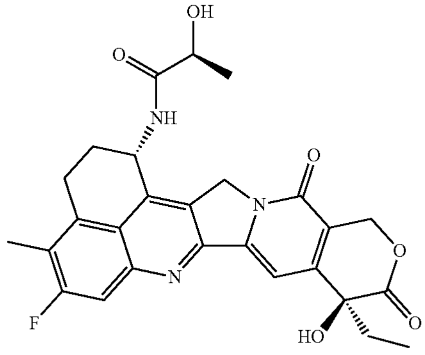

Compound 2

Dissolve compound 1 (Exatecan mesylate, purchased) (40 mg, 75.3 mmol, 1.0 eq) and L-lactic acid (10 mg, 113.0 mmol, 1.5 eq) in dry 5 mL DMF, and then add PyBop (58.8 mg, 113.0 mmol, 1.5 eq) and DIEA (15.7 uL, 113.0 mmol, 1.5 eq). After stirring for 3 hours at room temperature, the reaction was detected by TLC, quenched with water, extracted with dichloromethane (10 mL×3), the organic phases was combined, dried over anhydrous sodium sulfate, filtered, the filtrate was concentrated under reduced pressure, and the residue was purified by column chromatography to yield compound 2 (30.9 mg, 81.1%. LC-MS: $[M+H]^+$: 508.2. $^1H$ NMR (400 MHz, $CDCl_3/CD_3OD$): 0.91-0.94 (3H, m), 1.32-1.39 (3H, m), 1.71-1.83 (2H, m), 2.31 (3H, s), 2.78-3.02 (2H, m), 3.16-3.26 (2H, m), 4.27-4.35 (1H, m), 4.81-4.92 (1H, m), 5.15-5.24 (2H, m), 5.49-5.76 (2H, m), 7.52 (1H, d, J=12.0 Hz), 7.58 (1H, s), 7.75 (1H, d, J=12.0 Hz).

Example 2

Synthesis of Compound 4

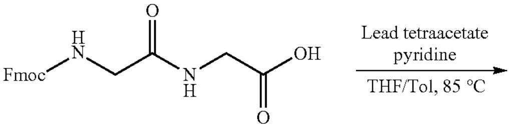

Compound 3

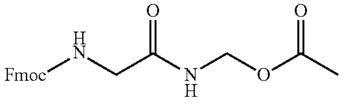

Compound 4

Add compound 3: N-fluorenylmethoxycarbonyl-glycyl-glycine (10 g, 28.2 mmol, 1.0 eq), lead tetraacetate (17.5 g, 55.3 mmol, 1.4 eq), 200 mL dry tetrahydrofuran and 67 mL toluene into a 500 mL single-necked flask, stirred evenly, protected by nitrogen, and heated to 85° C. to react for 2.5 h. TLC monitoring, after the reaction of the raw materials, cooled to room temperature, filtered, the filtrate was concentrated under reduced pressure, and the residue was purified by column chromatography to obtain compound 4 (8.7 g, 83.7%)).

Example 3

Synthesis of Compound 5

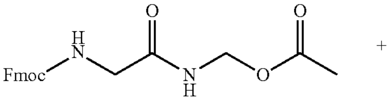

Compound 4

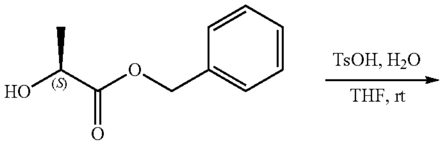

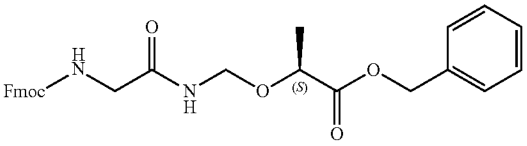

Compound 5

Add compound 4 (500 mg, 1.4 mmol, 1.0 eq), p-toluenesulfonic acid monohydrate (26 mg, 0.1 mmol, 0.1 eq) and 10 mL THE in a 25 mL single-necked flask, stirred well, reduced to 0° C., and then slowly add L-Benzyl lactate (1.2 g, 7.0 mmol, 5 eq), after the addition, warmed to room temperature. Monitoring by TLC, after the reaction, saturated $NaHCO_3$ solution was added, extracted with ethyl acetate, dried over anhydrous sodium sulfate, filtered, and concentrated. The residue was purified by reverse phase column to obtain compound 5 (400 mg, 60.3%). $^1H$ NMR (400 MHz, $CDCl_3$): 1.39 (3H, d, J=6.8 Hz), 3.78 (2H, t, J=4.0 Hz), 4.17-4.27 (2H, m), 4.42 (2H, d, J=4.0 Hz), 4.72-4.85 (2H, m), 5.11-5.58 (2H, m), 5.43 (1H, s), 7.06 (1H, t, J=8.0 Hz), 7.25-7.33 (6H, m), 7.38 (2H, t, J=8.0 Hz), 7.57 (2H, d, J=8.0 Hz), 7.75 (2H, d, J=8.0 Hz).

Example 4

Synthesis of Compound 6

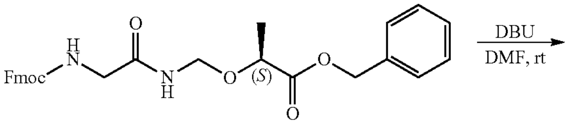

Compound 5

-continued

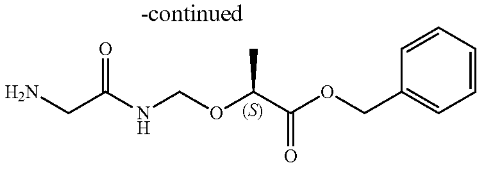

Compound 6

Add compound 5 (400 mg, 0.8 mmol, 1.0 eq) and 10 mL DMF into a 25 mL single-necked flask, stirred evenly, reduced to 0° C., and then slowly add DBU (137 mg, 0.9 mmol, 1.1 eq), and warmed to room temperature after the addition is complete reacted. Monitored by TLC, after the reaction, reactants were concentrated to obtain the crude compound 6 (550 mg), which was directly used in the next step without further purification.

Example 5

Synthesis of Compound 7

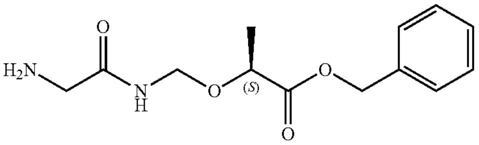

Compound 6

+

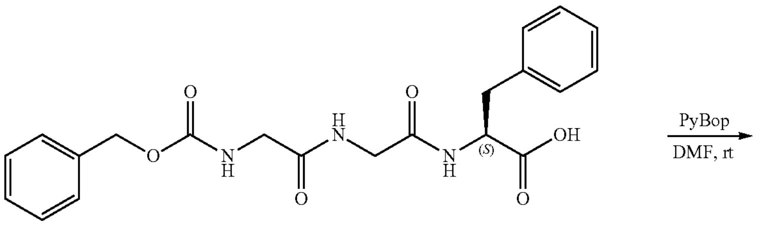

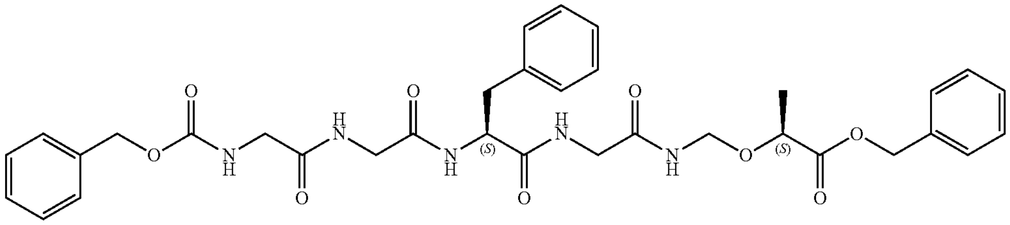

Compound 7

Z-Gly-Gly-Phe-OH (372 mg, 0.9 mmol, 1.1 eq), PyBOP (852 mg, 1.6 mmol, 2.0 eq) and 3 mL DMF were added to a 25 mL single-necked flask, stirred at room temperature for 5 minutes, and then added the crude compound 6 (550 mg), reacted at room temperature, monitored by HPLC. After the reaction was completed, water was added, the reaction was extracted with ethyl acetate, dried over anhydrous sodium sulfate, filtered, and concentrated. The residue was purified by reverse phase column to obtain compound 7 (326 mg, 59.2%).

Example 6

Synthesis of Compound 8

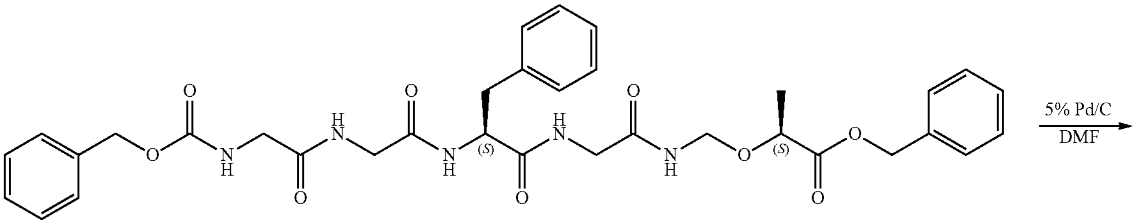

Compound 7

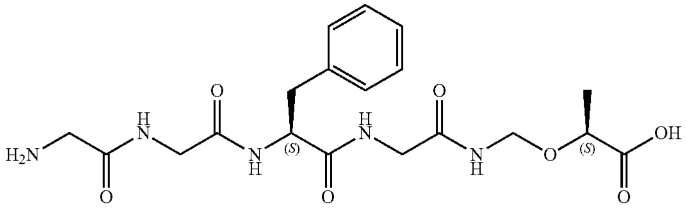

Compound 8

Compound 7 (50 mg, 1.0 eq, 0.08 mmol), 5% Pd/C (50 mg), 3 mL DMF was added to a 25 mL single-necked flask, and hydrogenation reaction was performed at room temperature. It was monitored by HPLC. After the reaction was completed, water was added and filtered, and the filtrate was concentrated to obtain the crude compound 8 (52 mg), which was directly used in the next step without purification.

Example 7

Synthesis of Compound 9

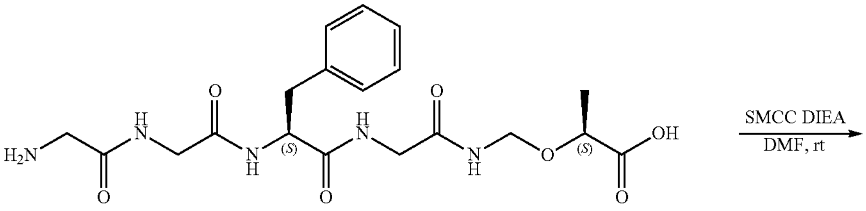

Compound 8

-continued
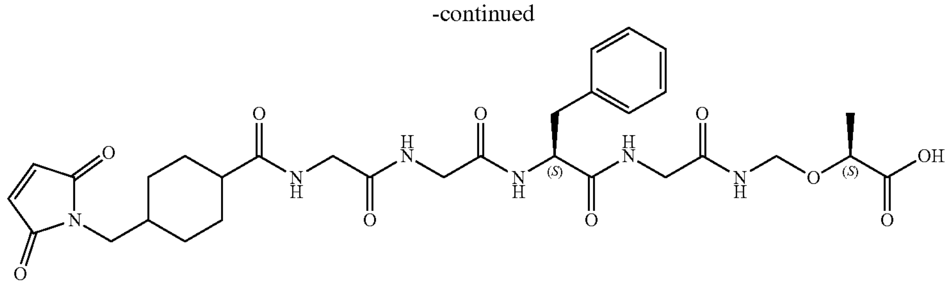
Compound 9
Compound 8 (52 mg), SMCC (23 mg, 0.07 mmol, 1.0 eq), DIEA (22.2 mg, 0.24 mmol, 2.5 eq) and 3 mL DMF were added to a 25 mL single-necked flask. Reacted at room temperature, monitored by HPLC, performing preparation, purification, and lyophilization to obtain the compound 9 (9.0 mg, 18.1%). MS: $[M-H]^{-}$=655.1.
Example 8
Synthesis of Compound 11
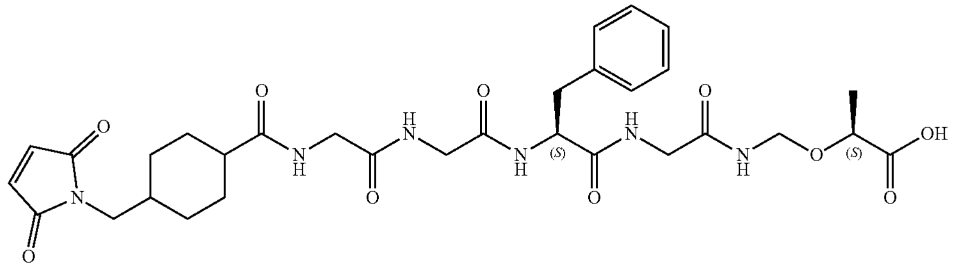
Compound 10
+
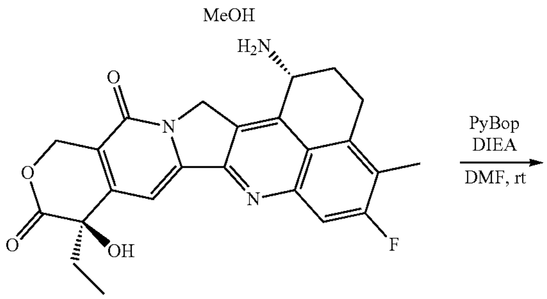
Compound 1

-continued

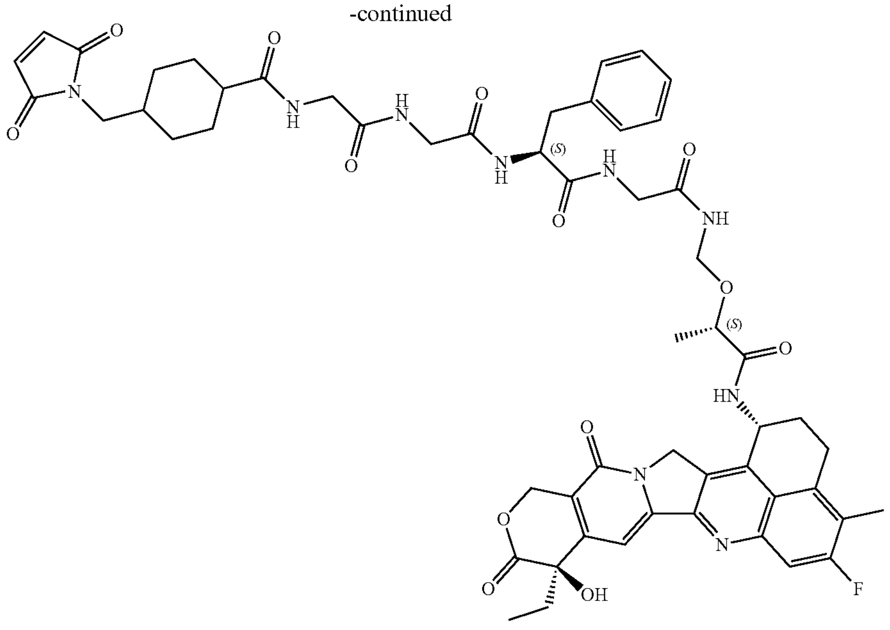

Compound 11

Add compound 9 (9.0 mg, 0.014 mmol, 1.0 eq), exatecan mesylate (6.6 mg, 0.014 mmol, 1.0 eq), and PyBOP (14.3 mg, 0.028 mmol, 2.0 eq) into a 25 mL single-necked flask, DIEA (6.2 mg, 0.048 mmol, 3.5 eq) and 0.5 mL DMF were reacted at room temperature, monitored by HPLC, perform preparation, purification and lyophilized to obtain compound 11 (7.0 mg, 48.3%). TOF: $[M+Na]^+=1096.42$.

Example 9

Synthesis of Compound 12 and Compound 13

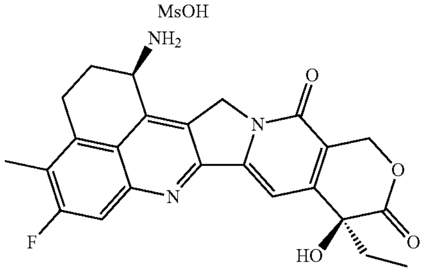

Compound 1

+

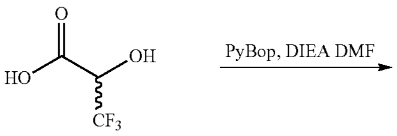

-continued

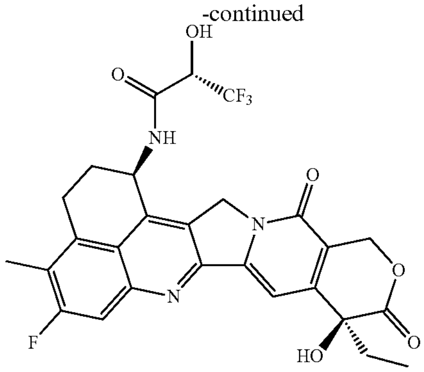

Compound 12

+

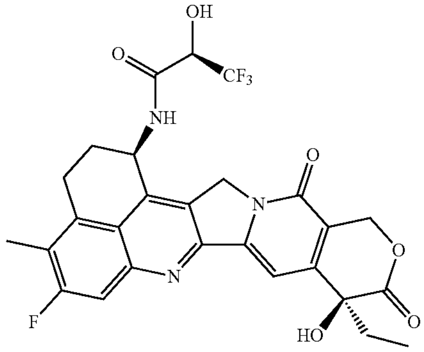

Compound 13

Compound 1 (exatecan mesylate) (40 mg, 75.3 mmol, 1.0 eq) and trifluorolactic acid (16.3 mg, 113.0 mmol, 1.5 eq) were dissolved in 5 mL dry DMF, and then PyBop (58.8 mg, 113.0 mmol, 1.5 eq) and DIEA (15.7 uL, 113.0 mmol, 1.5 eq) were added. After stirring at room temperature for 3 hours, TLC was used to detect that the reaction was completed, quenched with water, extracted with dichloromethane (10 mL×3), combined the organic phases, dried over anhydrous sodium sulfate, filtered, and concentrated the filtrate under reduced pressure. The residue was purified by column chromatography. Compound 12 (13.5 mg, 32%) was obtained. LC-MS: $[M+H]^+$=562.2. $^1H$ NMR (400 MHz, $CDCl_3/CD_3OD$): 0.91-0.95 (3H, m), 1.78-1.84 (2H, m), 2.34 (3H, s), 3.04-3.14 (2H, m), 3.27-3.32 (2H, m), 4.42-4.47 (1H, m), 5.08-5.20 (3H, m), 5.41-5.58 (2H, m), 7.23-7.25 (1H, m), 7.52-7.55 (1H, m); compound 13 (15.5 mg, 36.7%). LC-MS: $[M+H]^+$=562.2. $^1H$ NMR (400 MHz, $CDCl_3/CD_3OD$): 0.90-1.00 (3H, m), 1.74-1.89 (2H, m), 2.34 (3H, s), 3.01-3.09 (2H, m), 3.32-3.38 (2H, m), 4.65-4.71 (1H, m), 4.89-4.96 (1H, m), 5.17-5.30 (2H, m), 5.55-5.65 (2H, m), 7.53-7.61 (2H, m).

Example 10

Synthesis of Compound 14

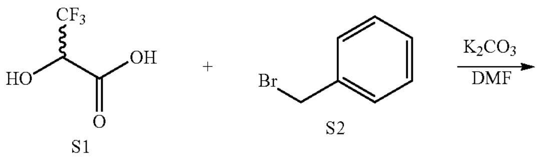

S1

S2

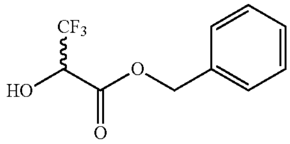

Compound 4

Dissolve trifluorolactic acid (3.5 g, 24.3 mmol, 1.0 eq) and $K_2CO_3$ (5.0 g, 36.5 mmol, 1.5 eq) in 35 mL dry DMF, add dropwisely benzyl bromide (5.0 g, 29.2 mmol, 1.2 eq) under ice-water bath, under nitrogen atmosphere, after the addition, warmed to room temperature and reacted for 5 hours. TLC detects that the reaction is completed, quenched with water, extracted with dichloromethane (100 mL×3), combined the organic phases, washed with saturated brine, and dried with anhydrous sodium sulfate. After filtering, the filtrate was concentrated under reduced pressure, and the residue was purified by column chromatography to obtain compound 14 (3.14 g, 55%). $^1H$ NMR (400 MHz, DMSO-$d_6$): 4.91-4.94 (1H, m), 5.25 (2H, s), 7.17-7.19 (1H, d), 7.39 (5H, s).

Example 11

Synthesis of Compound 15

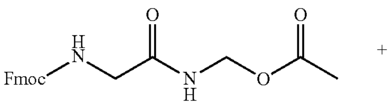

Compound 4

-continued

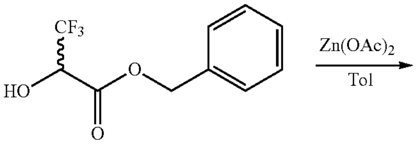

Compound 14

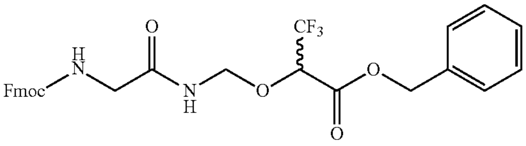

Compound 15

Add compound 4 (1.45 g, 3.9 mmol, 1.0 eq), compound 14 (1.84 g, 7.8 mmol, 2.0 eq), $Zn(OAc)_2$ (1.44 g, 7.86 mmol, 2.0 eq) and 25 mL toluene into a 50 mL single-necked flask under nitrogen atmosphere, after stirred evenly, the temperature was raised to 100° C. and reacted for 5.5 h. TLC monitoring showed that the product spot was obvious, filtered, and the filtrate was concentrated to obtain a yellow oil (4.0 g). The crude product was purified by column chromatography to obtain compound 15 (0.99 g, 46%). $^1H$ NMR (400 MHz, $CDCl_3$): 3.68-3.83 (2H, m), 4.20-4.23 (1H, m), 4.49 (2H, d, J=8.0 Hz), 4.73-4.78 (1H, m), 4.89-5.00 (2H, m), 5.19 (1H, s), 5.25 (2H, s), 7.11 (1H, s,), 7.29-7.35 (7H, m), 7.43 (2H, t, J=8.0 Hz), 7.59 (2H, d, J=8.0 Hz), 7.79 (2H, d, J=8.0 Hz).

Example 12

Synthesis of Compound 16

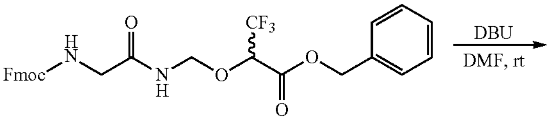

Compound 15

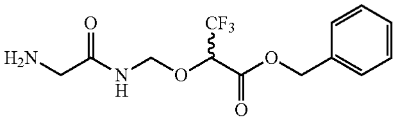

Compound 16

Add compound 15 (990 mg, 1.8 mmol, 1.0 eq) and 10 mL DMF in a 25 mL single-necked flask, stirred well, reduced to 0° C., and then slowly add DBU (335 mg, 2.2 mmol, 1.2 eq) under nitrogen atmosphere, after the addition is completed, continue the reaction at 0° C. for 30 minutes. TLC monitoring, the reaction of the raw materials is completed, and the reaction solution is directly used in the next step.

Example 13

Synthesis of Compound 17

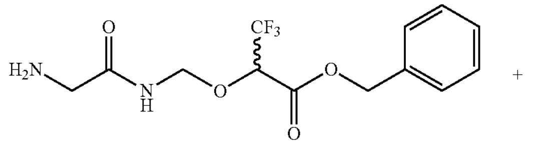

Compound 16

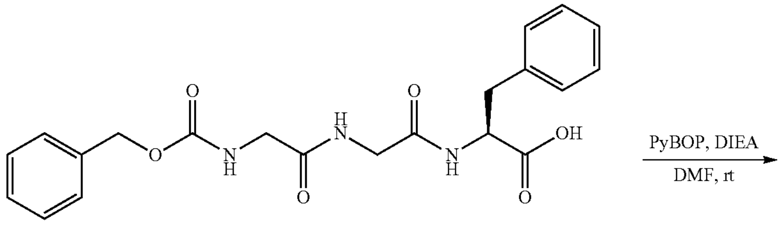

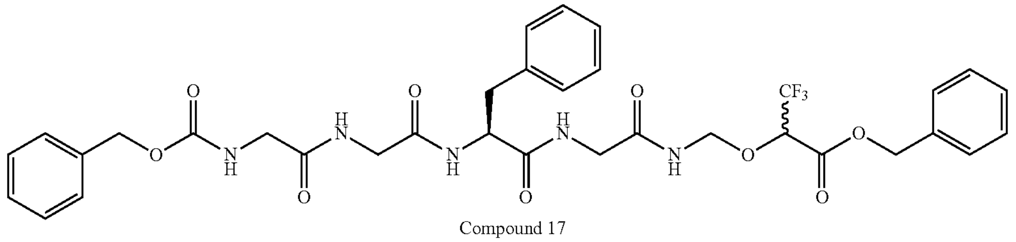

Compound 17

Add Z-Gly-Gly-Phe-OH (909 mg, 2.2 mmol, 1.2 eq), PyBOP (1.4 g, 2.7 mmol, 1.5 eq) and 10 mL DMF to a 50 mL single-necked bottle, add DIEA dropwisely under ice water bath, under nitrogen atmosphere, The reaction was continued for 10 mins, and the compound 16 solution was slowly added dropwise to the reaction solution under an ice-water bath. After the addition, the reaction solution was raised to room temperature and reacted for 1.5 h. The reaction was monitored by HPLC. After the reaction was completed, the preparation was purified and lyophilized to obtain compound 17 (0.91 g, 71%).

Example 14

Synthesis of Compound 18

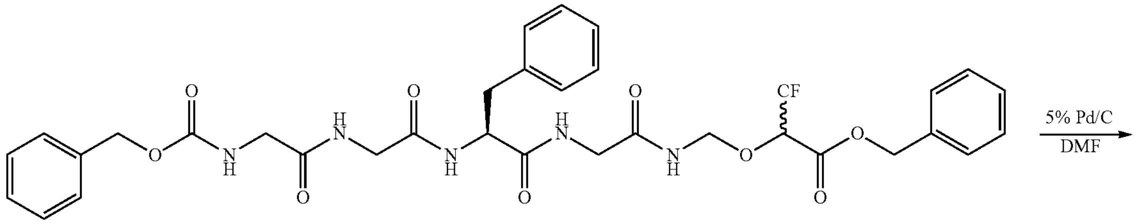

Compound 17

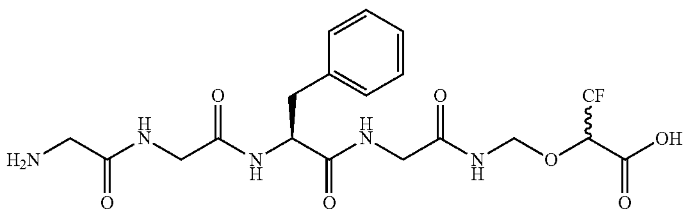

Compound 18

Compound 17 (85 mg, 1.0 eq, 0.12 mmol), 5% Pd/C (85 mg), 6 mL DMF was added to a 25 mL single-necked flask, and the reaction was hydrogenated at room temperature for 1 h. HPLC monitoring, the reaction of the raw materials is completed, the reaction liquid is filtered, and the filtrate is directly used for the next reaction.

Example 15

Synthesis of Compound 19

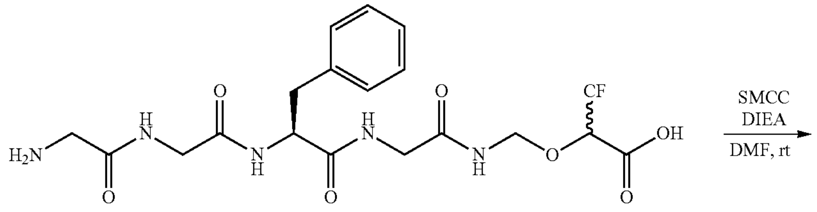

Compound 18

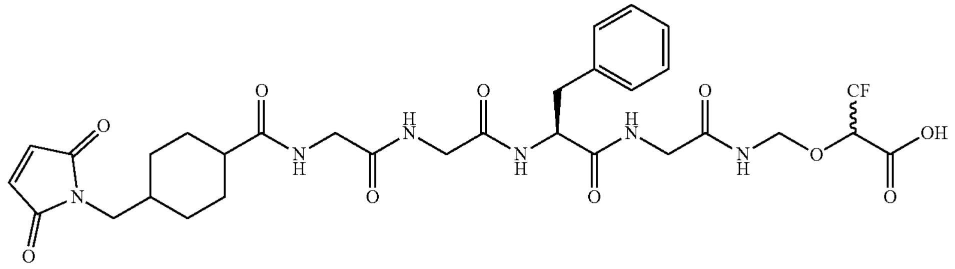

Compound 19

The compound 18 solution was filtered into a 25 mL single-necked flask, and SMCC (80 mg, 0.24 mmol, 2.0 eq), DIEA (62 mg, 0.48 mmol, 4.0 eq) were sequentially added under ice-water bath under nitrogen. After the addition, the temperature was raised to room temperature. Reacted for 1 hour, HPLC monitoring, the reaction were prepared, purified, lyophilized to obtain compound 19 (66 mg, 78%), MS: $[M-H]^-$=709.2.

Example 16

Synthesis of Compound 20 and Compound 21

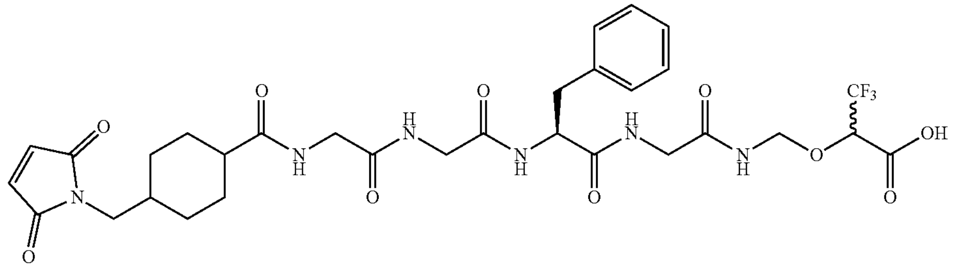

+

Compound 19

-continued

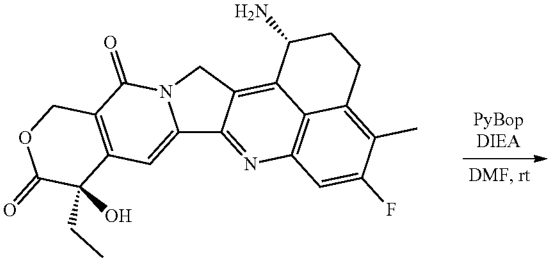

Compound 1

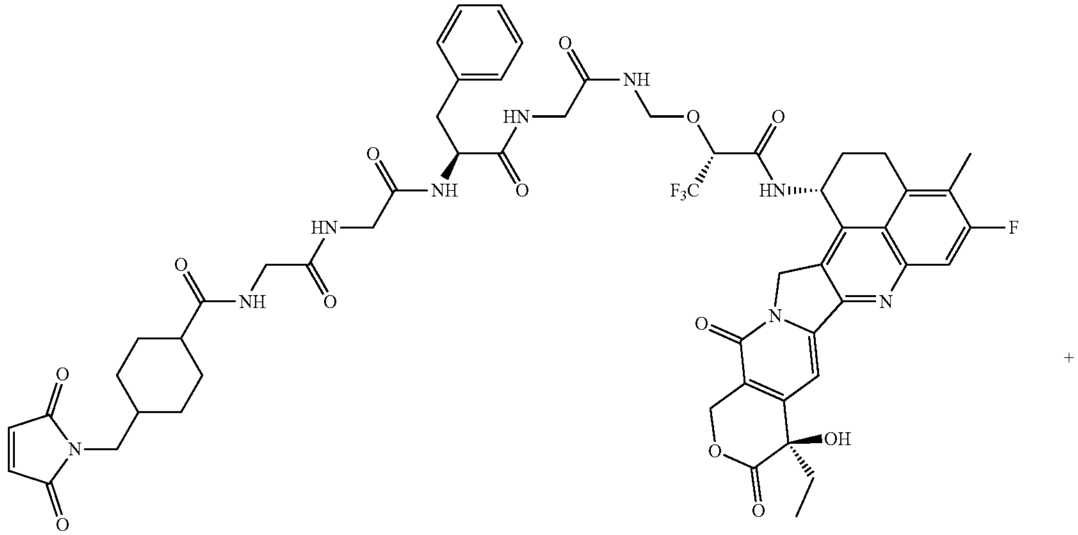

Compound 20

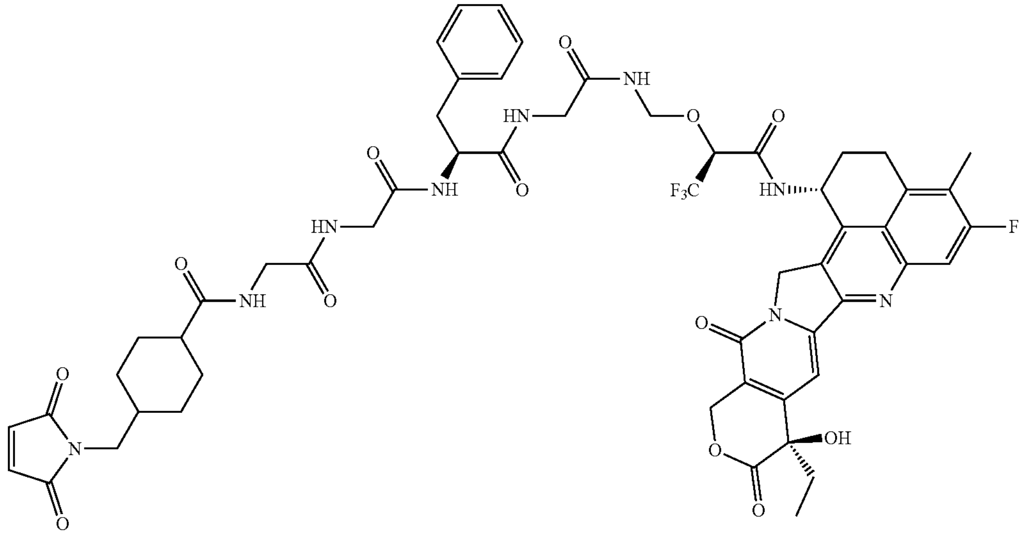

Compound 21

Dissolve compound 19 (10 mg, 14 umol, 1.0 eq), compound 1 (9 mg, 21 umol, 1.5 eq) and PyBop (14.6 mg, 28 mmol, 2.0 eq) in dry DMF (0.5 mL), under ice water bath add DIEA (5 uL, 28 umol, 2.0 eq) under nitrogen. After addition, it was heated to room temperature and reacted for 1 hour. HPLC monitored. The reaction of raw material compound 19 was completed. The reaction solution was directly prepared with HPLC pure water to obtain compound 20 (2.77 mg, 17.5). %), LC-MS: $[M+H]^+$=1128.0; Compound 21 (3.92 mg, 24.8%), LC-MS: $[M+H]^+$=1128.0

Example 17

Synthesis of Compound 22

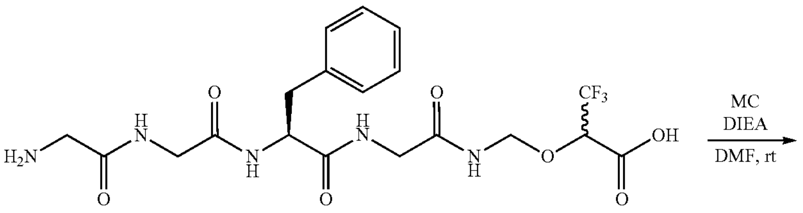

Compound 18

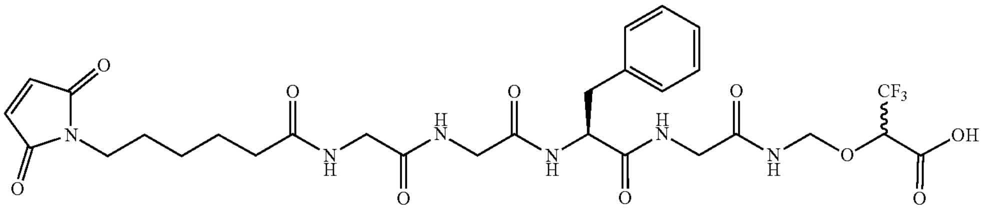

Compound 22

The compound 18 solution (0.15 mmol, 1.0 eq) was filtered into a 25 mL single-necked flask. Under ice water bath, MC (93 mg, 0.3 mmol, 2.0 eq), DIEA (78 mg, 0.6 mmol, 4.0 eq) were sequentially added, under nitrogen, the temperature was raised to room temperature and reacted for 1 h, monitored by HPLC, purified by pure water, and lyophilized to obtain compound 22 (90 mg, 86%), MS: $[M-H]^-$=683.2.

Example 18

Synthesis of Compound 23 and Compound 24

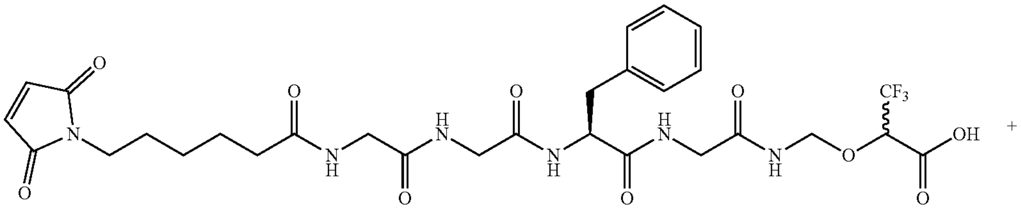

Compound 22

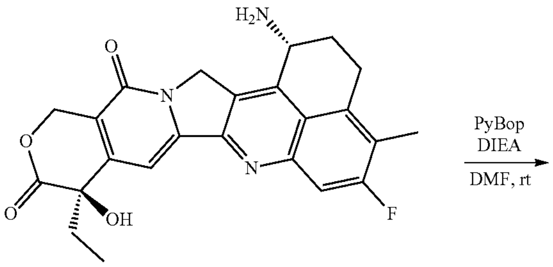

Compound 1

-continued

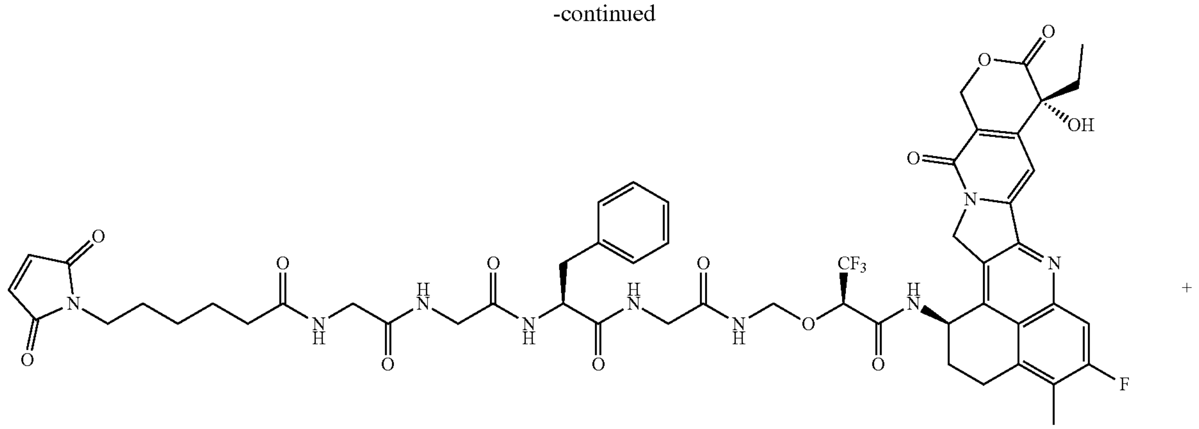

Compound 23

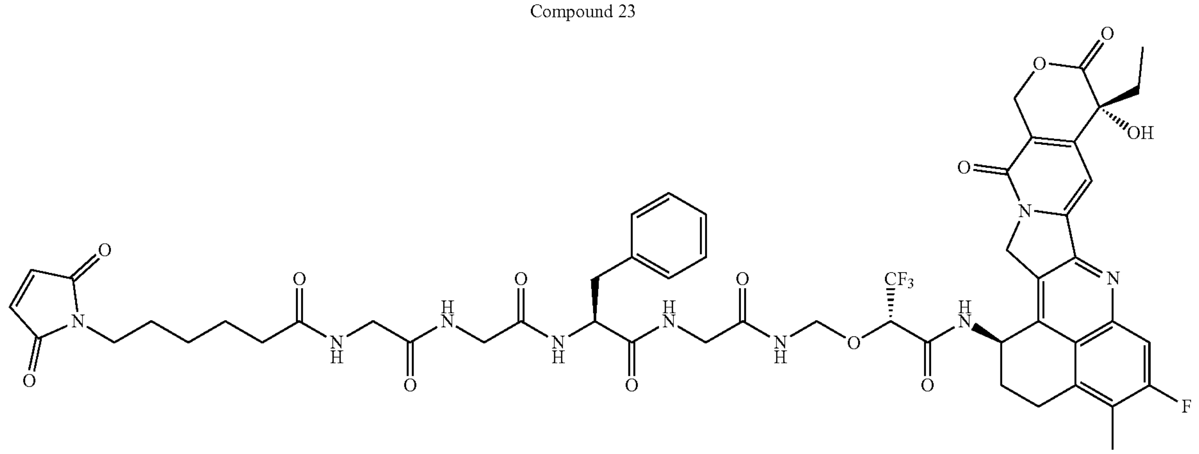

Compound 24

Dissolve compound 22 (15 mg, 21.9 umol, 1.0 eq), compound 1 (14.3 mg, 32.8 umol, 1.5 eq) and PyBop (22.8 mg, 43.8 mmol, 2.0 eq) in dry DMF (0.8 mL). Under ice water bath add DIEA (7.3 uL, 43.8 umol, 2.0 eq) under nitrogen. After addition, warmed to room temperature to react for 1 h, HPLC monitoring, the raw material compound 22 is reacted, the reaction solution is directly prepared with HPLC pure water to obtain compound 23 (6.01 mg, 25%), LC-MS: $[M+H]^+=1102.0$; and compound 24 (5.57 mg, 23.2%), LC-MS: $[M+H]^+=1102.0$.

Example 19

Synthesis of Compound 25

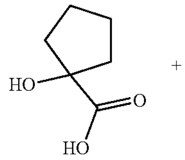

-continued

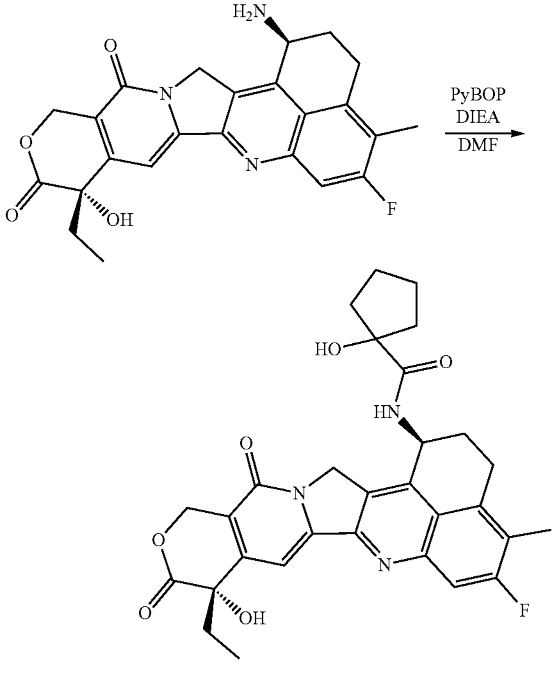

Compound 25

Add mandelic acid (42 mg, 0.09 mmol, 1.1 eq), exatecan (35 mg, 0.08 mmol, 1.0 eq), PyBOP (84 mg, 0.16 mmol, 2.0 eq), DIEA (36.4 mg, 0.28 mmol) to a 5 mL single-necked bottle, 3.5 eq) and 1 mL DMF, carry out the reaction at room temperature, HPLC monitored, preparation and purification, and lyophilization to obtain compound 25 (15.0 mg, 32.6%). $^1$H NMR ($CDCl_3$, 400 MHz) δ 7.70 (d, 1H, J=8.0 Hz), 7.64 (s, 1H), 5.64-5.75 (m, 2H), 5.48-5.38 (m, 1H), 5.29-5.21 (m, 1H), 5.19-5.11 (m, 1H), 3.37-3.11 (m, 2H), 2.55-2.38 (m, 4H), 2.32-2.15 (m, 2H), 2.08-1.99 (m, 1H), 1.94-1.85 (m, 4H), 1.33-1.24 (m, 4H), 1.05 (t, 3H, J=7.2 Hz); LC-MS: $[M+H]^+$=548.4.

Example 20

Synthesis of Compound 26

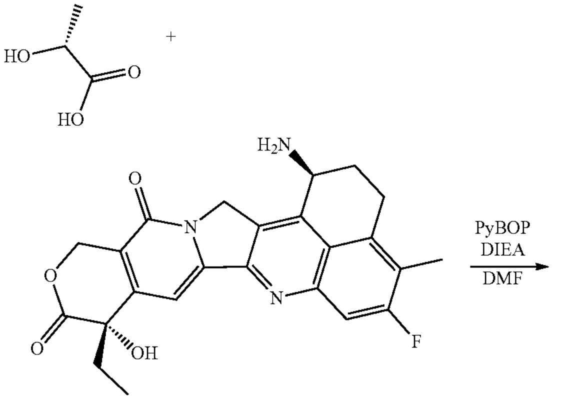

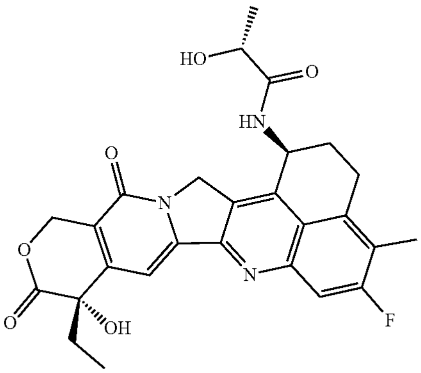

Compound 26

Add D-lactic acid (11.2 mg, 0.08 mmol, 1.1 eq), exatecan (30.0 mg, 0.07 mmol, 1.0 eq), PyBOP (119.5 mg, 0.14 mmol, 2.0 eq), DIEA (31.2 mg, 0.25 mmol, 3.5 eq) and 1 mL DMF, carry out the reaction at room temperature, HPLC monitoring, preparation and purification, and freeze-drying to obtain compound 26 (7.2 mg, 20.6%). $^1$H NMR ($CDCl_3$, 400 MHz) δ 7.75 (d, 1H, J=10.4 Hz), 7.70 (s, 1H), 5.75-5.63 (m, 2H), 5.46-5.38 (m, 1H), 5.30-5.16 (m, 2H), 4.50-4.40 (m, 1H), 3.34-3.13 (m, 2H), 2.50-2.36 (m, 3H), 2.34-2.21 (m, 1H), 2.05-2.02 (s, 1H), 1.96-1.84 (m, 2H), 1.35-1.23 (m, 3H), 1.06 (t, 3H, J=4.0 Hz); LC-MS: $[M+H]^+$=508.3.

Example 21

Synthesis of Compound 27

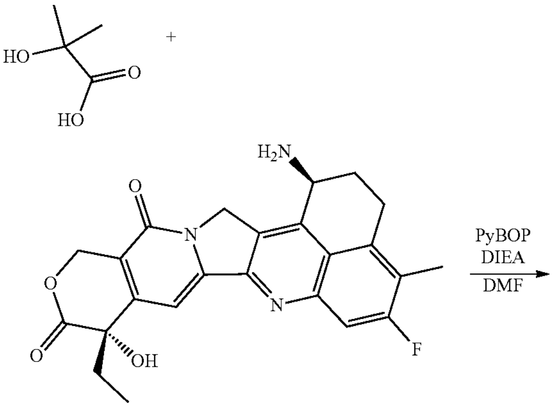

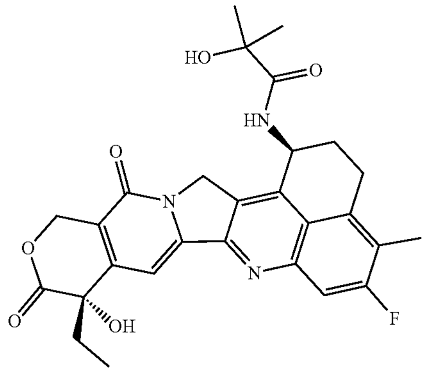

Compound 27

Add 2-methyllactic acid (10.5 mg, 0.10 mmol, 1.1 eq), exatecan (40 mg, 0.09 mmol, 1.0 eq), PyBOP (95.6 mg, 0.18 mmol, 2.0 eq), DIEA (41.4 mg, 0.32 mmol, 3.5 eq) and 1 mL DMF, reacted at room temperature, monitored by HPLC, prepared and purified, and lyophilized to obtain compound 27 (10.0 mg, 20.8%). $^1$H NMR ($CDCl_3$, 400 MHz) δ 7.68 (d, 1H, J=24 Hz), 7.63 (s, 1H), 5.77-5.59 (m, 2H), 5.48-5.39 (m, 1H), 5.30-5.22 (m, 1H), 5.19-5.11 (m, 1H), 3.33-3.10 (m, 2H), 2.24 (s, 3H), 1.71-1.63 (m, 2H), 1.58-1.52 (m, 2H), 1.40-1.20 (m, 6H), 1.05 (t, 3H, J=7.2 Hz); LC-MS: $[M+H]^+$= 522.2.

Example 22

Synthesis of Compound 28

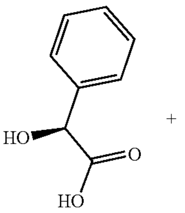

-continued

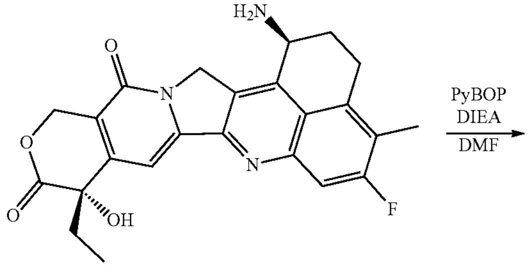

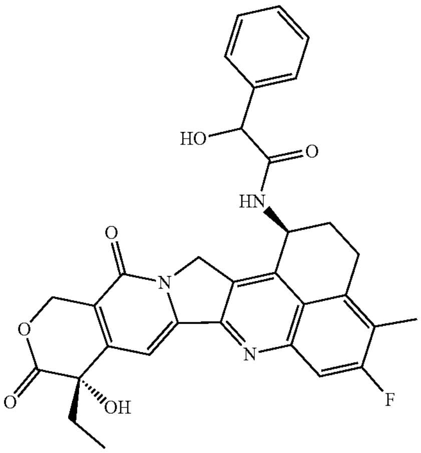

Compound 28

Add R—(−)-mandelic acid (15.2 mg, 0.10 mmol, 1.1 eq), exatecan (40 mg, 0.09 mmol, 1.0 eq), PyBOP (95.6 mg, 0.18 mmol, 2.0 eq) into a 5 mL single-necked bottle, DIEA (41.4 mg, 0.32 mmol, 3.5 eq) and 1 mL DMF, carrying out reaction at room temperature, HPLC monitoring, preparation and purification, and freeze-drying to obtain compound 28 (12.2 mg, 23.3%). $^1$H NMR ($CDCl_3$, 400 MHz) δ7.76 (d, 1H, J=8.0 Hz), 7.69 (s, 1H), 7.53-7.35 (m, 5H), 5.77-5.70 (m, 1H), 5.65-5.55 (m, 1H), 5.34-5.20 (m, 4H), 3.32-3.31 (m, 2H), 2.47-2.40 (m, 3H), 2.30-2.27 (m, 1H), 2.05-2.02 (s, 1H), 1.93-1.89 (m, 3H), 1.07 (t, 3H, J=8.0 Hz); LC-MS: $[M+H]^+$=570.2.

Example 23

Synthesis of Compound 29

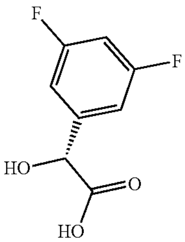

+

-continued

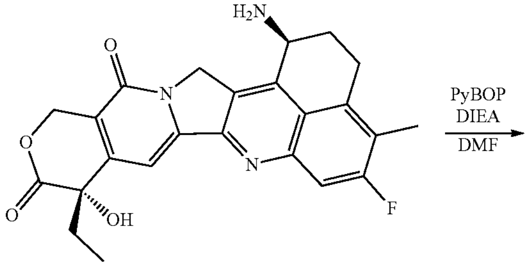

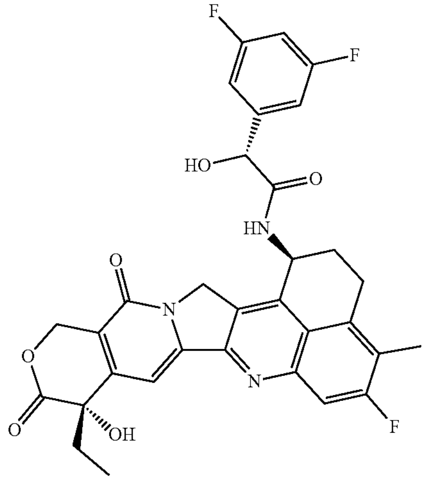

Compound 29

Add 3,5-difluoromandelic acid (23.7 mg, 0.13 mmol, 1.1 eq), exatecan (50 mg, 0.11 mmol, 1.0 eq), and PyBOP (119.5 mg, 0.23 mmol, 2.0 eq) into a 5 mL single-necked bottle, DIEA (37.1 mg, 0.29 mmol, 2.5 eq) and 1 mL DMF, carry out reaction at room temperature, HPLC monitoring, preparation and purification, and lyophilization to obtain compound 29 (13.5 mg, 19.4%). $^1$H NMR (DMSO, 400 MHz) δ8.76 (d, 1H, J=8.4 Hz), 7.81 (d, 1H, J=10.8 Hz), 7.31 (s, 1H), 7.27-7.07 (m, 4H), 5.54-5.47 (m, 1H), 5.43 (s, 2H), 5.20-5.03 (m, 4H), 3.20-3.09 (m, 2H), 2.43-2.38 (m, 3H), 2.17-2.09 (m, 1H), 1.96-1.79 (m, 3H), 0.88 (t, 3H, J=7.2 Hz); LC-MS: $[M+H]^+$=606.2.

Example 24

Synthesis of Compound 30

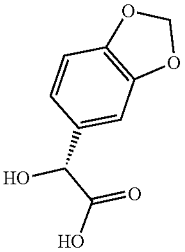

+

-continued

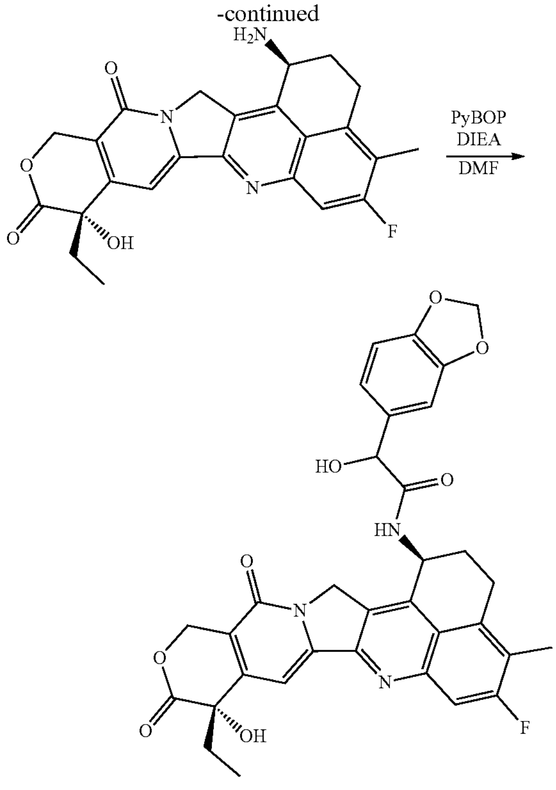

Compound 30

Add 3,5-difluoromandelic acid (22.5 mg, 0.13 mmol, 1.1 eq), exatecan (50 mg, 0.11 mmol, 1.0 eq), and PyBOP (119.5 mg, 0.23 mmol, 2.0 eq) into a 5 mL single-necked bottle, DIEA (37.1 mg, 0.29 mmol, 2.5 eq) and 1 mL DMF, carry out reaction at room temperature, HPLC monitoring, preparation and purification, and lyophilization to obtain compound 30 (8.2 mg, 11.7%). $^1$H NMR (DMSO, 400 MHz) δ8.60 (d, 1H, J=8.4 Hz), 7.79 (d, 1H, J=11.2 Hz), 7.31 (s, 1H), 7.02-6.90 (m, 2H), 6.90-6.72 (m, 1H), 6.05-5.93 (m, 2H), 5.52-5.40 (m, 2H), 5.19-5.09 (m, 1H), 5.09-4.92 (m, 2H), 2.98-2.85 (m, 2H), 2.22-2.14 (m, 3H), 1.94-1.83 (m, 1H), 1.75-1.59 (m, 1H), 1.53-1.45 (m, 2H), 0.66 (t, 3H, J=7.2 Hz); LC-MS: $[M+H]^+$=614.2.

Example 25

Synthesis of Compound 31

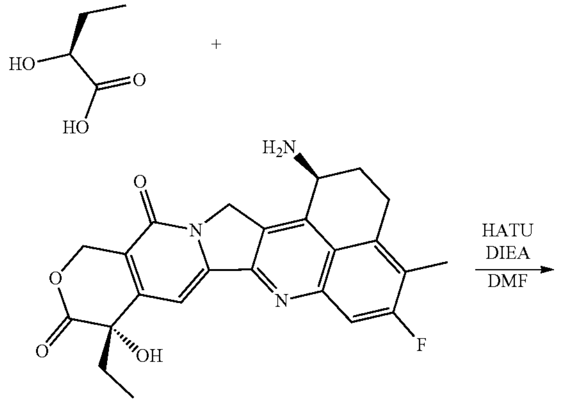

-continued

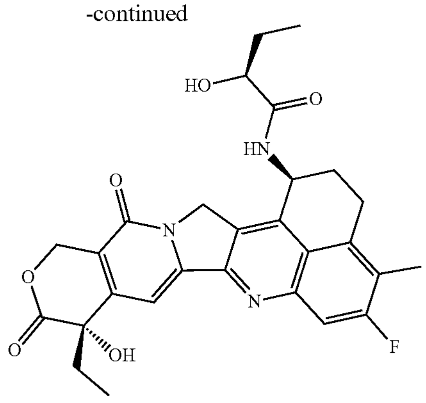

Compound 31

Add S-2-hydroxybutyric acid (16.3 mg, 0.16 mmol, 1.1 eq), exatecan (68.0 mg, 0.16 mmol, 1.0 eq), HATU (59.4 mg, 0.16 mmol, 1.0 eq) into a 5 mL single-necked bottle, DIEA (50.5 mg, 0.39 mmol, 2.5 eq) and 1 mL DMF, carry out reaction at room temperature, HPLC monitoring, preparation and purification, lyophilization to obtain compound 31 (16.3 mg, 20.1%). $^1$H NMR (DMSO, 400 MHz) δ8.36 (d, 1H, J=8.8 Hz), 7.79 (d, 1H, J=11.2 Hz), 7.31 (s, 1H), 6.53 (s, 1H), 5.60-5.52 (m, 1H), 5.46-5.40 (m, 3H), 5.24-5.17 (m, 2H), 3.23-3.09 (m, 2H), 2.45-2.38 (m, 3H), 2.28-2.08 (m, 2H), 1.94-1.80 (m, 2H), 1.79-1.66 (m, 1H), 1.66-1.55 (m, 1H), 1.05-0.84 (m, 6H); LC-MS: $[M+H]^+$=522.3.

Example 26

Camptothecin Drug Cellular Activity Test

The cytotoxic activity of camptothecin drugs was determined by the following experimental process: Camptothecin drugs were added to cell culture media that grows human tumors cells that express A431, Fadu, Bxpc-3 (EGFR-positive cells) and U87-MG, SW620 (negative control cells). Cell survival rates were measured after the cells were cultured for 72 hours. Cell-based in vitro experiments are used to determine cell survival rate, cytotoxicity, and programmed cell death induced by the camptothecin drug of the present application.

The in vitro efficacy of the camptothecin drugs was determined by cell proliferation test. CellTiter 96® Aqueous One Solution Cell Proliferation Assay is commercially available (Promega Corp., Madison, WI). CellTiter 96® AQueous One Solution Cell Proliferation Assay(a) is a colorimetric method to detect the number of living cells in cell proliferation and cytotoxicity experiments. This reagent contains a novel tetrazolium compound [3-(4, 5-dimethyl-thiazol-2-yl)-5-(3-carboxymethoxyphenyl)-2-(4-sulfophenyl)-2H-tetrazolium, inner salt; MTS] and an electronic coupling agent (phenazine ethosulfate; PES). PES has enhanced chemical stability, which allows it to be mixed with MTS to form a stable solution. This convenient "single solution" mode is an improvement on the basis of the first generation CellTiter 96® AQueous Assay. The electronic coupling agent PMS and MTS solution used in the CellTiter 96® AQueous Assay are provided separately. MTS (Owen's reagent) is reduced by cell organisms into a colored formazan product (Illustration 1), which can be directly dissolved in the culture medium. The conversion in all likelihood is completed under the action of NADPH or NADH produced by dehydrogenases in metabolically active cells. When testing, just add a small amount of CellTiter 96® AQueous One Solution Reagent directly to the culture plate well, incubate for 1-4 hours, and then read the absorbance value at 490 nm with a microplate reader.

Illustration 1

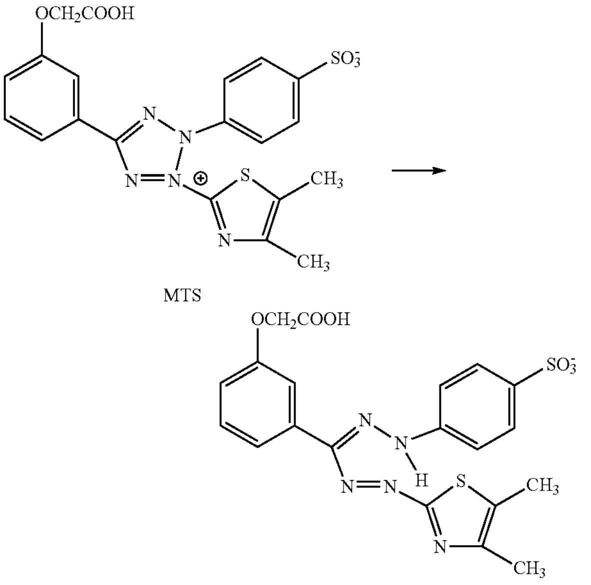

MTS

Formazan

The amount of formazan detected at 490 nm is directly proportional to the number of viable cells in culture. Since the formazan product of MTS is soluble in tissue culture medium, CellTiter 96® AQueous One Solution Assay has fewer steps than MTT or INT methods.

In the present application, A431, Fadu, Bxpc-3 (EGFR positive expressing cells) and U87-MG, SW620 (negative control cells) are used as the research system for in vitro drug efficacy detection. In a 96-well plate, use an appropriate cell density for plating, and after 24 hours, add camptothecin. After 24 hours, dilute the camptothecin drug with the test medium (1 uM start, 5-fold dilution, 9 concentrations, add test medium in the tenth column as a blank control), and add the diluted camptothecin drug to the corresponding cell wells. The cell wells were then shaken with a microplate shaker (model: MX100-4A) for 3 minutes at a shaking speed of 550 rpm/min. After shaking, they were placed in a carbon dioxide incubator and incubated for 3 days. After 3 days, add 20 uL MTS (Promega, G3581) to each well for 2 hours, and the microplate reader (Molecular Device, model: SpectraMAX190) reads at 490 nM. By detecting the activity of dehydrogenase in mitochondria, the inhibitory effect of camptothecin drugs on cell proliferation was evaluated.

| | Cell Viability (nm) | | | | |
|---|---|---|---|---|---|
| Compounds | Fadu | BXPC-3 | A431 | U87-MG | SW620 |
| SN38 | 42.14 | 119.85 | 13.62 | 15.65 | 3.28 |
| 2 | 11.09 | 38.82 | 40.93 | 7.4 | 10.43 |
| 12 | 0.002 | 1.6 | 15.47 | 0.06 | 0.06 |
| 13 | 0.06 | 40.02 | 6.37 | 0.32-1.6 | 1.06 |
| 25 | 41.03 | 15.79 | 11.67 | 10.41 | 1.50 |
| 28 | 14.25 | 80.98 | 5.12 | 18.34 | 11.90 |
| 29 | 41.29 | 90.10 | 19.55 | 23.61 | 2.15 |

-continued

| | Cell Viability (nm) | | | | |
|---|---|---|---|---|---|
| Compounds | Fadu | BXPC-3 | A431 | U87-MG | SW620 |
| 30 | 19.23 | 34.21 | 19.88 | 29.90 | 2.25 |
| 31 | 17.52 | 55.41 | 14.78 | 10.80 | 17.53 |

SN38 is a classic highly active camptothecin drug and has been clinically proven in IMMU-132 ADC. Through cell viability experiments, the application proved that the camptothecin derivatives of the present application showed equivalent or higher activity against cell viability than SN38 in the representative tumor cells Fadu, BXPC-3, A431, U87-MG, and SW620.

Example 27

General Coupling Method for ADC Preparation.

After a preliminary purification, the antibody molecule C with monomer ratio greater than 95% is buffer-exchanged to 10 mg/mL with an ultrafiltration centrifuge tube into a phosphate buffer solution. Add TCEP at the amount of 20 times the number of moles of the antibody molecules, and react for 4 hours at room temperature to open the disulfide bonds between the antibody chains. Add a payload that is 20 times the number of moles of the antibody and react for 2 hours at room temperature. After the reaction is over, use an ultrafiltration centrifuge tube with a molecular weight cut-off of 30 KDa to exchange the liquid into PBS, and remove uncoupled payload. After changing the liquid, the ADC sample is filtered with a 0.22 micron sterile filter for later use. The compounds 11, 20, 21, 23, and 24 were coupled to the antibody molecule C using the general coupling method described in Example 27.

| Compounds | Coupling ADC number |
|---|---|
| 11 | C-11 |
| 20 | C-20 |
| 21 | C-21 |
| 23 | C-23 |
| 24 | C-24 |

Example 28

ADC Anti-Tumor Cell Activity Measurement

Similar to the cell activity test method for camptothecin drugs, the present application uses A431, Fadu, Bxpc-3 (antigen-positive expressing cells), and SW620 (antigen-negative control cells) as the research system for in vitro drug efficacy measurement. In a 96-well plate, use an appropriate cell density for plating, and after 24 hours, the ADC drugs are added. After 24 hours, dilute the ADC drug with detection medium (1 uM starting, 5-fold dilution, 9 concentrations, add detection medium in the tenth column as a blank control), add the diluted ADC drug to the corresponding cell wells Use a microplate shaker (model: MX100-4A) to shake for 3 minutes at a shaking speed of 550 rpm/min. After shaking, place it in a carbon dioxide incubator and incubate for 3 days. After 3 days, add 20 uL MTS (Promega, G3581) to each well for 2 hours, and read at 490 nM by a microplate reader (Molecular Device, model: SpectraMAX190). By detecting the activity of dehydrogenase in mitochondria, the inhibitory effect of ADC drugs on cell proliferation was measured.

| | Cell Viability (nm) | | | |
|---|---|---|---|---|
| Compounds | Fadu | BXPC-3 | A431 | SW620 |
| C-11 | 12.44 | 242.09 | 27.86 | 221.24 |
| C-20 | 3.98 | 186.98 | 30.74 | 85.16 |
| C-21 | 2.49 | 86.97 | 8.15 | 48.17 |
| C-23 | 4.74 | 25.18 | 11.16 | 154.40 |
| C-24 | 4.09 | 15.79 | 11.67 | 1.50 |

As measured by the above ADC cell activity tests, the camptothecin drugs of the present application, after being coupled to the antibody through the linking unit L, show excellent and/or improved anti-tumor activity in multiple antigen-positive tumor cell lines, and have great clinical significance.

Example 29

ADC In Vivo Drug Efficacy Test

In the present application, a tumor-bearing A431 mouse model is established to evaluate the in vivo efficacy of ADC drugs. In one embodiment, $3\times10^6$ A431 cells were injected subcutaneously into the right side of BALB/c nude mice aged 4-6 weeks. After the average tumor size of the mice grew to 140-150 $mm^3$, they were randomly divided into groups, 5 in each group. Blank control (buffer solution blank) and the antibody-drug conjugate C-11 were administered intravenously at a dose of 10 mg/kg on day 0, 7, 14, 21 respectively. The tumor volume measurement data is displayed as the average tumor volume±SE at the time of measurement, and the weight change of the mice is recorded at the same time to monitor the preliminary toxicity of the ADC drugs in vivo.

As shown in the above drug efficacy experiments in ADC mice, the data show that the camptothecin drug of the present application, after being coupled to antibody through the linking unit L, exhibits clear anti-tumor activity in tumor-bearing mice, and the average tumor body volume is significantly lower than the blank control. The body weight of the mice did not change significantly during the administration period, and no mice died in the group. The camptothecin drugs of the present application demonstrates good safety.

What is claimed is:

1. A camptothecin compound having the general formula I or its pharmaceutically acceptable salts thereof:

I

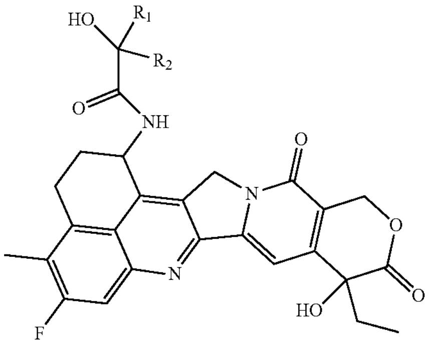

wherein $R_1$ and $R_2$ each is independently selected from the group consisting of $C_1$-$C_3$ alkyl or substituted alkyl, —H, aryl, substituted aryl or heteroaryl; or $R_1$ and $R_2$ together with the carbon atoms to which they are attached form cyclobutane, cyclopentane or cyclohexane; and $R_1$ and $R_2$ are not hydrogen at the same time.

2. The camptothecin compound or its pharmaceutically acceptable salts thereof according to claim 1, having a formula selected from the following formulae (a), (b), or (c):

| | Mice body weight | | | | | | |
|---|---|---|---|---|---|---|---|
| group | D0 | D3 | D7 | D10 | D13 | D16 | D20 |
| blank control | 16.4 ± 0.31 | 17.4 ± 0.32 | 18.3 ± 0.47 | 18.5 ± 0.42 | 18.9 ± 0.45 | 18.9 ± 0.35 | 19.5 ± 0.33 |
| C-11 | 17.6 ± 0.16 | 18.2 ± 0.14 | 18.8 ± 0.31 | 19.2 ± 0.29 | 19.6 ± 0.30 | 19.9 ± 0.28 | 20.1 ± 0.39 |

| | Average Volume of Tumor ($mm^3$) | | | | | | |
|---|---|---|---|---|---|---|---|
| group | D0 | D3 | D7 | D10 | D13 | D16 | D20 |
| blank control | 152.0 ± 16.22 | 296.0 ± 38.14 | 621.6 ± 87.52 | 823.6 ± 71.51 | 1,028.0 ± 94.51 | 1,227.5 ± 98.30 | 1,526.5 ± 97.14 |
| C-11 | 147.4 ± 8.04 | 168.8 ± 6.76 | 256.5 ± 26.69 | 316.8 ± 35.44 | 352.8 ± 39.31 | 333.0 ± 79.16 | 347.2 ± 107.67 |

(a)

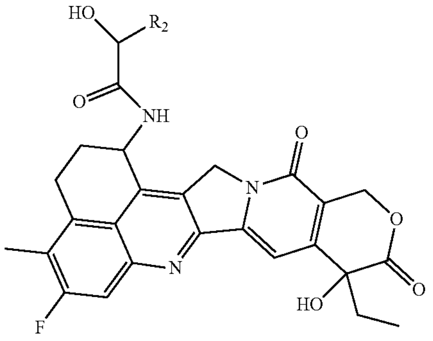

(b)

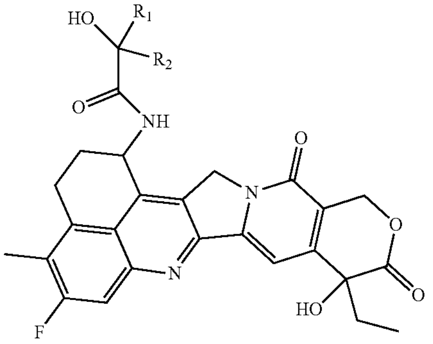

(c)

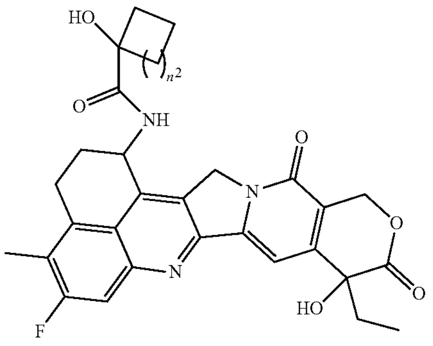

wherein $R_1$ is hydrogen, $R_2$ is $C_1$-$C_3$ alkyl, aryl, substituted aryl or heteroaryl as in formula (a); or $R_1$ and $R_2$ are $C_1$-$C_3$ alkyl, —$CF_3$, aryl, heteroaryl or substituted aryl as in formula (b); or $R_1$ and $R_2$ together with the carbon atoms to which they are connected form cyclohexane;

wherein in formula (a), $R_2$ is independently selected from —$(CH_2)n^1$-$CH_3$, aryl, heteroaryl, substituted aryl, where $n^1$=0, 1 or 2;

in formula (b), $R_1$ and $R_2$ are independently selected from —$(CH_2)n^1$-$CH_3$, —$CF_3$, aryl, heteroaryl, substituted aryl, where $n^1$=0, 1 or 2;

In formula (c), $R_1$ and $R_2$, together with the carbon atoms to which they are connected form cyclohexane, and $n^2$=3.

3. The camptothecin compound or pharmaceutically acceptable salts thereof according to claim 2, having a formula selected from the following formulae (a-1) or (a-2):

(a-1)

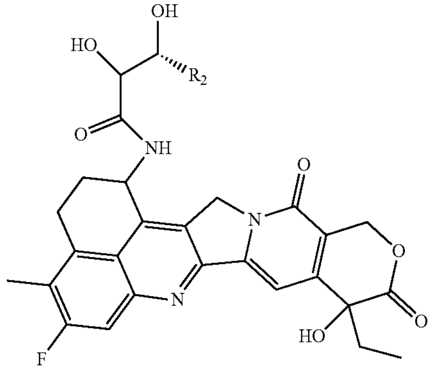

(a-2)

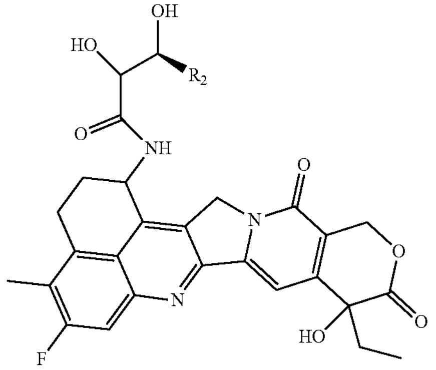

wherein $R_1$ is hydrogen, $R_2$ is independently selected from —$(CH_2)n^1$-$CH_3$, aryl, heteroaryl or substituted aryl, where $n^1$=0, 1 or 2;

wherein the carbon connected to $R_2$ has two configurations: R or S;

in formula (a-1), the carbon to which $R_2$ is attached is in the R configuration; and in formula (a-2), the carbon to which $R_2$ is attached is in the S configuration.

4. The camptothecin compound or its pharmaceutically acceptable salts thereof according to claim 1, wherein the substituted aryl comprises aryl groups having substituents selected from the group consisting of halogen, hydrocarbyl, alkoxy, hydroxyl, nitro, amino, hydroxyl and cyano.

5. The camptothecin compound or its pharmaceutically acceptable salts thereof according to claim 1, having a formula selected from the following formulae:

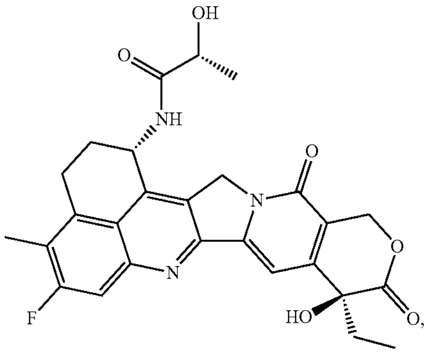

-continued
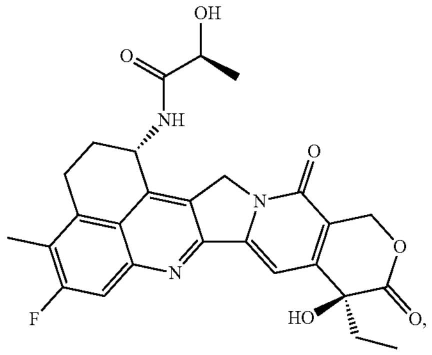
,
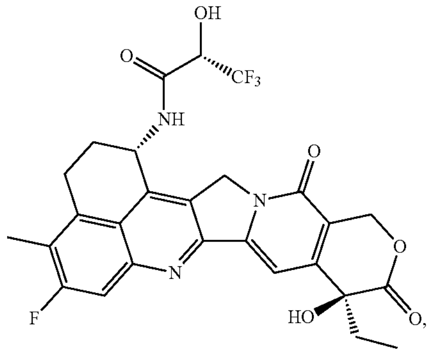
,
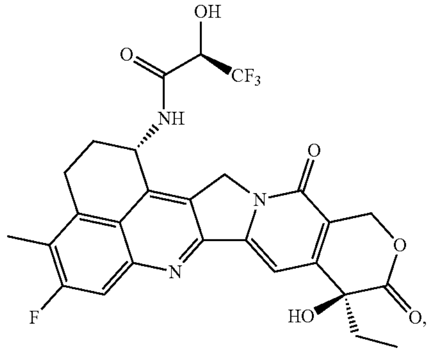
,
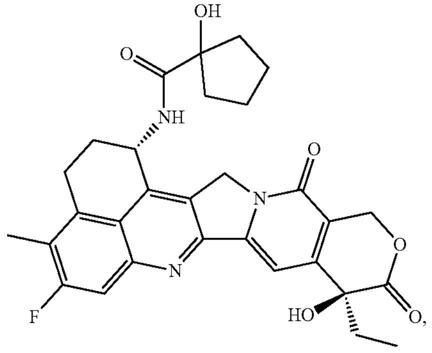
,
-continued
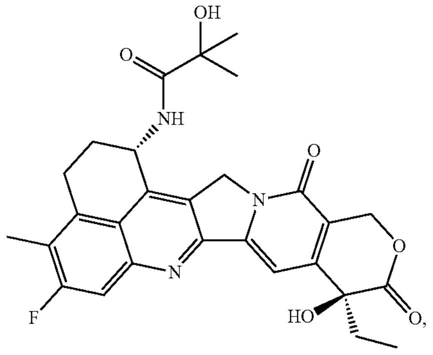
,
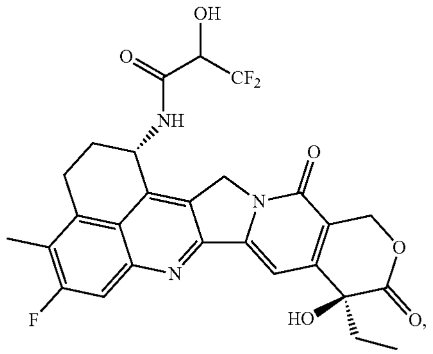
,
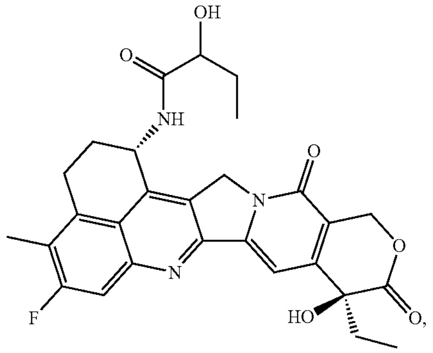
,
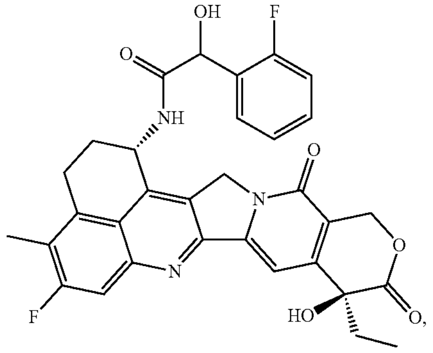
, -continued

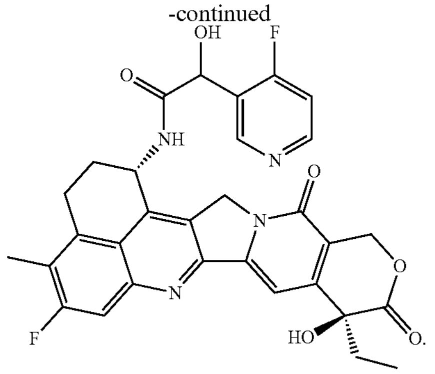

6. An antitumor drug for treating a solid tumor or a blood tumor, comprising the camptothecin compound or its pharmaceutically acceptable salts thereof according to claim 1, wherein the solid tumor or blood tumor comprises lung cancer, kidney cancer, colon cancer, rectal cancer, glioma multiforme, ovarian cancer, pancreatic cancer, breast cancer, melanoma, gastric cancer, or esophageal cancers.

7. An antibody-drug conjugate having a formula as shown in formula II, $$Ab\text{—}(L\text{—}D)_m \qquad \text{(II)}$$

wherein

Ab is an antibody moiety comprising an antibody, an antibody fragment or a protein;

L is a linker connecting the Ab at one end to the drug moiety (D) at the other end;

D is a drug moiety selected from the camptothecin compounds or its pharmaceutically acceptable salts thereof according to any of claims 1 to 6, wherein D is connected to L through a hydroxyl group on the D; and m is an integer ranging from 1-20; and wherein the antibody-drug conjugate is configured to exert its drug effect by releasing a drug moiety (D) after reaching a target cell.

8. The antibody-drug conjugate according to claim 7, wherein the connecting unit L is selected from the group consisting of —O—, —N(R)$n_1$-, —$CH_2$—, —CH(R)$n_1$-, amide, ester bond, —S—, and -(PEG)$n_2$-, wherein $n_1$ is an integer ranging from 1-3, $n_2$ is an integer ranging from 1-20.

9. The antibody-drug conjugate according to claim 7, wherein the antibody moiety has a binding specificity to a target cell of cancer or an autoimmune disease.

10. A pharmaceutical composition for treating a solid tumor or a blood tumor, comprising the antibody-drug conjugate according to claim 7, wherein the solid tumor or blood tumor comprises lung cancer, kidney cancer.

* * * * *